US012806034B2

(12) United States Patent
Glerum et al.

(10) Patent No.: US 12,806,034 B2
(45) Date of Patent: Nov. 24, 2026

(54) EXPANDABLE FUSION DEVICE AND METHOD OF INSTALLATION THEREOF

(71) Applicant: GLOBUS MEDICAL, INC., Audubon, PA (US)

(72) Inventors: Chad Glerum, Pennsburg, PA (US); Mark Weiman, Downingtown, PA (US); Andrew Iott, Newtown Square, PA (US); Mark Adams, Downingtown, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 19/215,556

(22) Filed: May 22, 2025

(65) Prior Publication Data

US 2026/0272669 A1 Sep. 17, 2026

Related U.S. Application Data

(60) Continuation of application No. 18/402,802, filed on Jan. 3, 2024, now Pat. No. 12,310,860, which is a (Continued)

(51) Int. Cl.

*A61F 2/44* (2006.01)
*A61F 2/46* (2006.01)
*A61F 2/30* (2006.01)

(52) U.S. Cl.

CPC ............ *A61F 2/4455* (2013.01); *A61F 2/442* (2013.01); *A61F 2/447* (2013.01); *A61F 2002/3008* (2013.01); *A61F 2002/30387* (2013.01); *A61F 2002/30448* (2013.01); *A61F 2002/30492* (2013.01); *A61F 2002/30507* (2013.01); *A61F 2002/30515* (2013.01);

(Continued)

(58) Field of Classification Search

CPC .. A61F 2/44; A61F 2/442; A61F 2/447; A61F 2/4455; A61F 2002/3008; A61F 2002/30387; A61F 2002/30448; A61F 2002/30492; A61F 2002/30507; A61F 2002/30515; A61F 2002/3052; A61F 2002/30523; A61F 2002/30538; A61F 2002/30545; A61F 2002/3055; A61F 2002/30556; A61F 2002/30579; A61F 2002/30777; A61F 2002/4677; A61F 2002/4629; A61F 2002/4475

USPC ............................................ 623/17.11–17.16

See application file for complete search history.

(56) References Cited

U.S. PATENT DOCUMENTS 6,176,882 B1 * 1/2001 Biedermann ........... A61F 2/447 623/17.11
6,454,807 B1 * 9/2002 Jackson .................. A61F 2/447 623/17.15

(Continued)

*Primary Examiner* — Jessica Weiss

(57) ABSTRACT

The present invention provides an expandable fusion device capable of being installed inside an intervertebral disc space to maintain normal disc spacing and restore spinal stability, thereby facilitating an intervertebral fusion. In one embodiment, the fusion device includes a body portion, a first endplate, and a second endplate, the first and second endplates capable of being moved in a direction away from the body portion into an expanded configuration or capable of being moved towards the body portion into an unexpanded configuration. The fusion device is capable of being deployed and installed in both configurations.

16 Claims, 32 Drawing Sheets

Related U.S. Application Data continuation of application No. 17/662,743, filed on May 10, 2022, now Pat. No. 11,890,203, which is a continuation of application No. 16/929,707, filed on Jul. 15, 2020, now Pat. No. 11,344,430, which is a continuation of application No. 15/926,021, filed on Mar. 20, 2018, now Pat. No. 10,744,002, which is a continuation of application No. 14/847,151, filed on Sep. 8, 2015, now Pat. No. 9,949,841, which is a division of application No. 13/667,812, filed on Nov. 2, 2012, now Pat. No. 9,155,628, which is a continuation-in-part of application No. 13/273,994, filed on Oct. 14, 2011, now Pat. No. 9,358,126, and a continuation-in-part of application No. 12/823,736, filed on Jun. 25, 2010, now Pat. No. 8,685,098, said application No. 13/273,994 is a continuation of application No. 12/579,833, filed on Oct. 15, 2009, now Pat. No. 8,062,375.

(52) U.S. Cl.

CPC ................. *A61F 2002/3052* (2013.01); *A61F 2002/30523* (2013.01); *A61F 2002/30538* (2013.01); *A61F 2002/30545* (2013.01); *A61F 2002/3055* (2013.01); *A61F 2002/30556* (2013.01); *A61F 2002/30579* (2013.01); *A61F 2002/30593* (2013.01); *A61F 2002/30777* (2013.01); *A61F 2002/30878* (2013.01); *A61F 2002/30904* (2013.01); *A61F 2002/4629* (2013.01); *A61F 2002/4677* (2013.01)

(56) References Cited

U.S. PATENT DOCUMENTS

| | | | | |
|---|---|---|---|---|
| 6,830,589 | B2 * | 12/2004 | Erickson | A61F 2/446<br>623/17.15 |
| 10,154,911 | B2 * | 12/2018 | Predick | A61B 17/8858 |
| 11,534,311 | B2 * | 12/2022 | Emerick | A61F 2/447 |
| 11,564,807 | B2 * | 1/2023 | Iott | A61F 2/447 |
| 2004/0087947 | A1 * | 5/2004 | Lim | A61F 2/4465<br>606/279 |
| 2005/0113916 | A1 * | 5/2005 | Branch, Jr. | A61F 2/447<br>623/17.11 |
| 2005/0125061 | A1 * | 6/2005 | Zucherman | A61F 2/4425<br>623/17.11 |
| 2006/0253201 | A1 * | 11/2006 | McLuen | A61F 2/4455<br>623/17.11 |
| 2008/0147193 | A1 * | 6/2008 | Matthis | A61F 2/4465<br>623/17.16 |
| 2011/0035011 | A1 * | 2/2011 | Cain | A61F 2/4425<br>623/17.16 |
| 2014/0243982 | A1 * | 8/2014 | Miller | A61F 2/447<br>623/17.16 |

* cited by examiner

EXPANDABLE FUSION DEVICE AND METHOD OF INSTALLATION THEREOF

CROSS-REFERENCE TO RELATED APPLICATIONS

The present application is a continuation of U.S. patent application Ser. No. 18/402,802 filed on Jan. 3, 2024 (published as U.S. Pat. Pub. No. 2024-0148519), which is a continuation of U.S. patent application Ser. No. 17/662,743 filed on May 10, 2022 (now U.S. Pat. No. 11,890,203), which is a continuation of U.S. patent application Ser. No. 16/929,707 (now U.S. Pat. No. 11,344,430), which is a continuation of U.S. patent application Ser. No. 15/926,021 filed on Mar. 20, 2018 (now U.S. Pat. No. 10,744,002), which is a continuation of U.S. patent application Ser. No. 14/847,151 filed on Sep. 8, 2015 (now U.S. Pat. No. 9,949,841), which is a divisional of U.S. patent application Ser. No. 13/667,812, filed on Nov. 2, 2012 (now U.S. Pat. No. 9,155,628), which (i) is a continuation-in-part of U.S. patent application Ser. No. 13/273,994, filed on Oct. 14, 2011 (now U.S. Pat. No. 9,358,126), which is a continuation of U.S. patent application Ser. No. 12/579,833, filed on Oct. 15, 2009 (now U.S. Pat. No. 8,062,375), and (ii) is a continuation-in-part of U.S. patent application Ser. No. 12/823,736, filed on Jun. 25, 2010 (now U.S. Pat. No. 8,685,098), the entire contents of which are incorporated herein by reference in their entireties for all purposes.

FIELD OF THE INVENTION

The present invention relates to the apparatus and method for promoting an intervertebral fusion, and more particularly relates to an expandable fusion device capable of being inserted between adjacent vertebrae to facilitate the fusion process.

BACKGROUND OF THE INVENTION

A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc is first partially or fully removed. An intervertebral fusion device is then typically inserted between neighboring vertebrae to maintain normal disc spacing and restore spinal stability, thereby facilitating an intervertebral fusion.

There are a number of known conventional fusion devices and methodologies in the art for accomplishing the intervertebral fusion. These include screw and rod arrangements, solid bone implants, and fusion devices which include a cage or other implant mechanism which, typically, is packed with bone and/or bone growth inducing substances. These devices are implanted between adjacent vertebral bodies in order to fuse the vertebral bodies together, alleviating the associated pain.

However, there are drawbacks associated with the known conventional fusion devices and methodologies. For example, present methods for installing a conventional fusion device often require that the adjacent vertebral bodies be distracted to restore a diseased disc space to its normal or healthy height prior to implantation of the fusion device. In order to maintain this height once the fusion device is inserted, the fusion device is usually dimensioned larger in height than the initial distraction height. This difference in height can make it difficult for a surgeon to install the fusion device in the distracted intervertebral space.

As such, there exists a need for a fusion device capable of being installed inside an intervertebral disc space at a minimum to no distraction height and for a fusion device that can maintain a normal distance between adjacent vertebral bodies when implanted.

SUMMARY OF THE INVENTION

In an exemplary embodiment, the present invention provides an expandable fusion device capable of being installed inside an intervertebral disc space to maintain normal disc spacing and restore spinal stability, thereby facilitating an intervertebral fusion. In one embodiment, the fusion device includes a body portion, a first endplate, and a second endplate. The first and second endplates are capable of being moved in a direction away from the body portion into an expanded configuration or capable of being moved towards the body portion into an unexpanded configuration. The expandable fusion device is capable of being deployed and installed in the unexpanded configuration or the expanded configuration.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

A spinal fusion is typically employed to eliminate pain caused by the motion of degenerated disk material. Upon successful fusion, a fusion device becomes permanently fixed within the intervertebral disc space. Looking at FIG. 1, an exemplary embodiment of an expandable fusion device 10 is shown between adjacent vertebral bodies 2 and 3. The fusion device 10 engages the endplates 4 and 5 of the adjacent vertebral bodies 2 and 3 and, in the installed position, maintains normal intervertebral disc spacing and restores spinal stability, thereby facilitating an intervertebral fusion. The expandable fusion device 10 can be manufactured from a number of materials including titanium, stainless steel, titanium alloys, non-titanium metallic alloys, polymeric materials, plastics, plastic composites, PEEK, ceramic, and elastic materials.

In an exemplary embodiment, bone graft or similar bone growth inducing material can be introduced around and within the fusion device 10 to further promote and facilitate the intervertebral fusion. The fusion device 10, in one embodiment, is preferably packed with bone graft or similar bone growth inducing material to promote the growth of bone through and around the fusion device. Such bone graft may be packed between the endplates of the adjacent vertebral bodies prior to, subsequent to, or during implantation of the fusion device.

Figure 2:
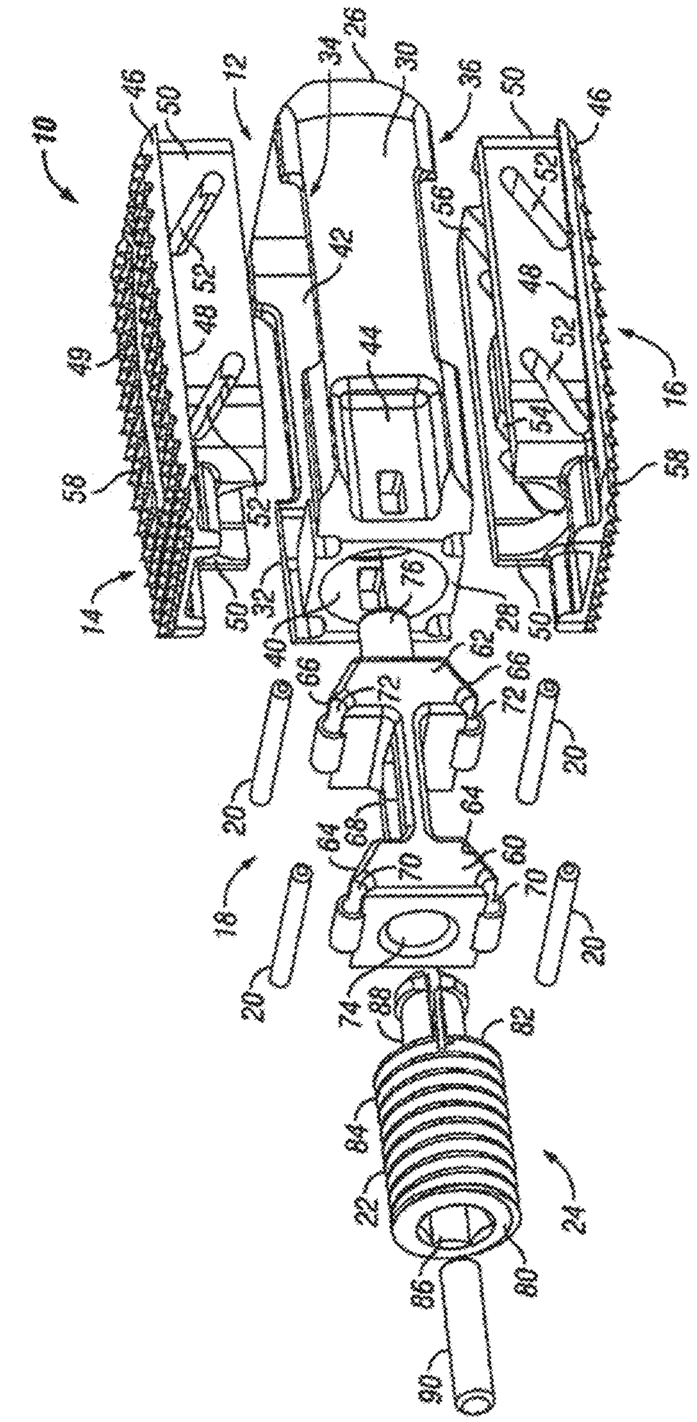
FIG. 2 is an exploded view of the expandable fusion device of FIG. 1.
Figure 3:
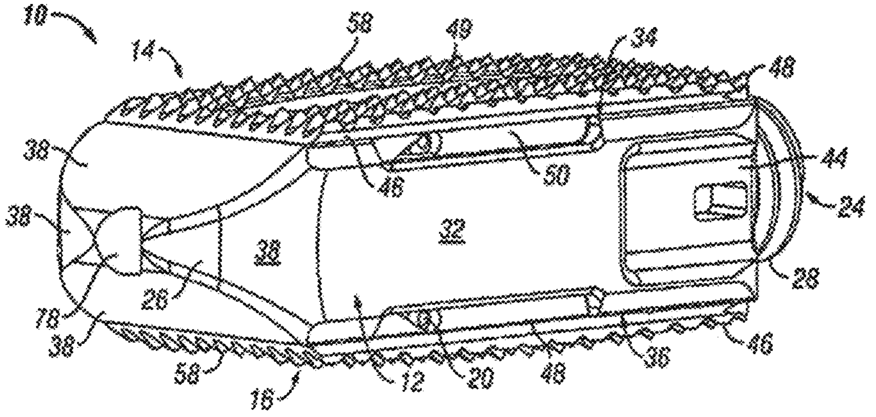
FIG. 3 is a front perspective view of the expandable fusion device of FIG. 1 shown in an unexpanded position

With reference to FIG. 2, an exploded perspective view of one embodiment of the fusion device 10 is shown. In an exemplary embodiment, the fusion device 10 includes a body portion 12, a first endplate 14, a second endplate 16, a translation member 18, a plurality of pins 20, an actuation member 22, and a locking mechanism 24.

With additional reference to FIGS. 3-8, in an exemplary embodiment, the body portion 12 has a first end 26, a second end 28, a first side portion 30 connecting the first end 26 and the second end 28, and a second side portion 32 connecting the first end 26 and the second end 28. The body portion 12 further includes an upper end 34, which is sized to receive at least a portion of the first endplate 14, and a lower end 36, which is sized to receive at least a portion of the second endplate 16.

The first end 26 of the fusion device 10, in an exemplary embodiment, includes at least one angled surface 38, but can include multiple angled surfaces. The angled surface can serve to distract the adjacent vertebral bodies when the fusion device 10 is inserted into an intervertebral space. In another preferred embodiment, it is contemplated that there are at least two opposing angled surfaces forming a generally wedge shaped to distract the adjacent vertebral bodies when the fusion device 10 is inserted into an intervertebral space.

The second end 28 of the body portion 12, in an exemplary embodiment, includes an opening 40 which may include threading. In another exemplary embodiment, the opening 40 may include ratchet teeth instead of threading. The opening 40 extends from the second end 28 of the body portion 12 into a central opening 42 in the body portion 12. In one embodiment, the central opening 42 is sized to receive the translation member 18 and the opening 40 is sized to threadingly receive the actuation member 22. In another exemplary embodiment, the opening 40 is sized to receive the actuation member 22 in a ratcheting fashion. In yet another exemplary embodiment, first side portion 30 and second side portion 32 each include a recess 44 located towards the second end 28 of the body portion 12. The recess 44 is configured and dimensioned to receive an insertion instrument (not shown) that assists in the insertion of the fusion device 10 into an intervertebral space.

Although the following discussion relates to the first endplate 14, it should be understood that it also equally applies to the second endplate 16 as the second endplate 16 is substantially identical to the first endplate 14. Turning now to FIGS. 2-11, in an exemplary embodiment, the first endplate 14 has an upper surface 46, a lower surface 48, and a through opening 49. The through opening 49, in an exemplary embodiment, is sized to receive bone graft or similar bone growth inducing material and further allow the bone graft or similar bone growth inducing material to be packed in the central opening 42 in the body portion 12.

Figure 4:
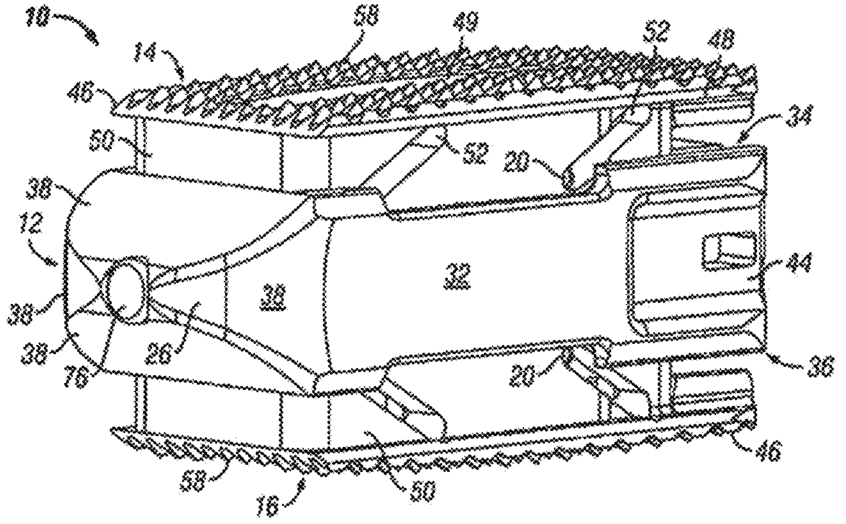
FIG. 4 is a front perspective view of the expandable fusion device of FIG. 1 shown in an expanded position.
Figure 5:
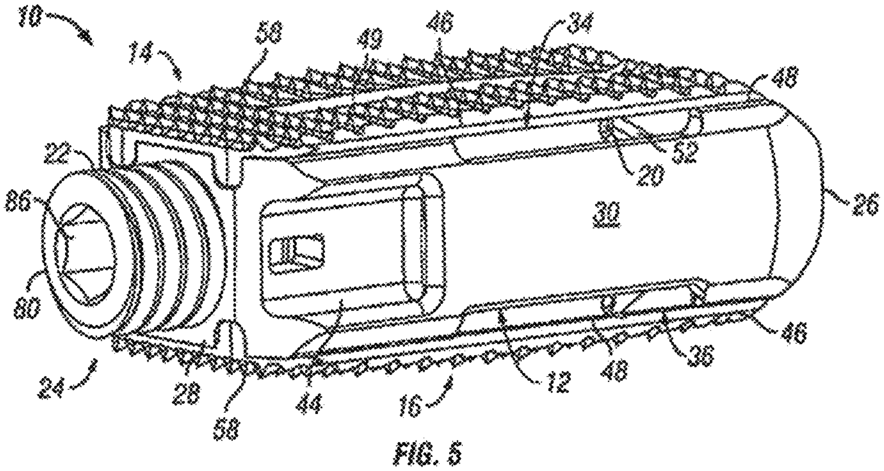
FIG. 5 is a rear perspective view of the expandable fusion device of FIG. 1 shown in an unexpanded position.
Figure 6:
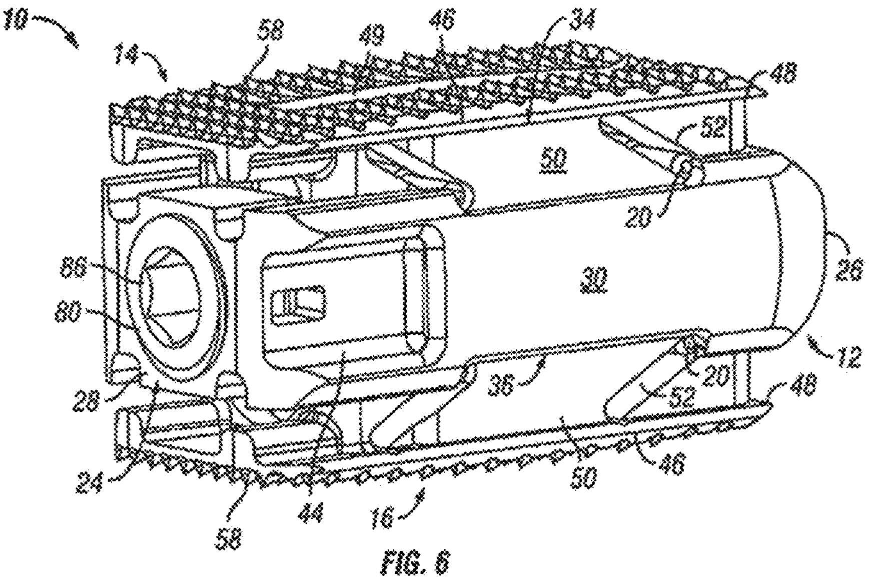
FIG. 6 is a rear perspective view of the expandable fusion device of FIG. 1 shown in an expanded position.
Figure 7:
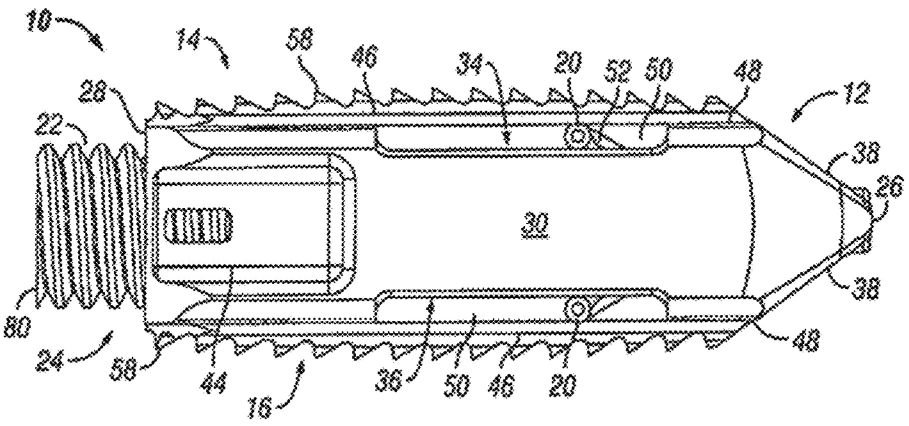
FIG. 7 is a side view of the expandable fusion device of FIG. 1 shown in an unexpanded position.
Figure 8:
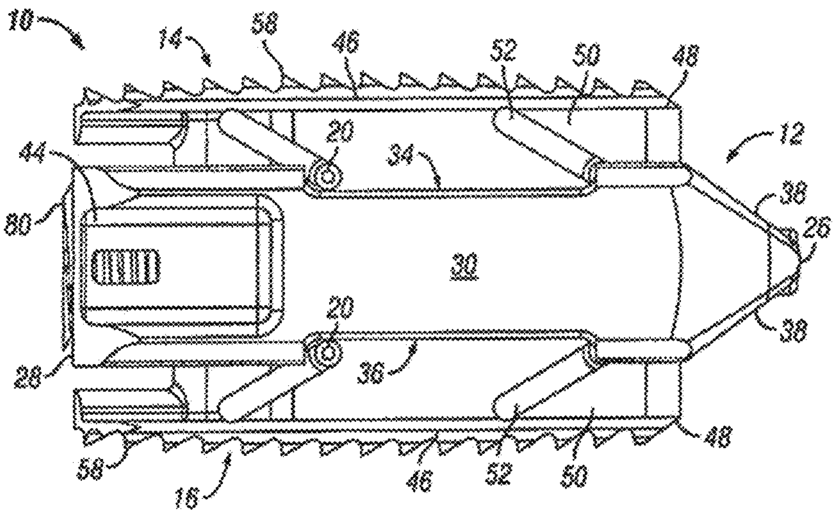
FIG. 8 is a side view of the expandable fusion device of FIG. 1 shown in an expanded position.
Figure 9:
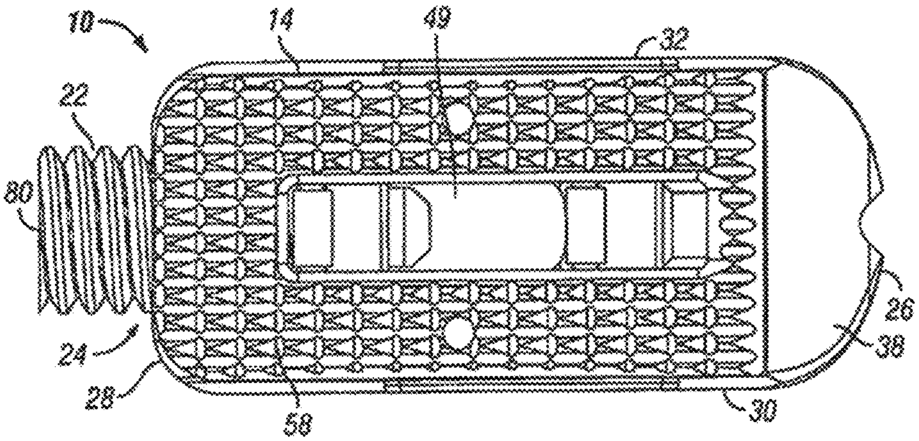
FIG. 9 is a top view of the expandable fusion device of FIG. 1.

In one embodiment, the lower surface 48 includes at least one extension 50 extending along at least a portion of the lower surface 48. As best seen in FIGS. 2 and 4, in an exemplary embodiment, the extension 50 can extend along a substantial portion of the lower surface 48, including, along each side of the endplate 14 and along the front end of the endplate 14. In another exemplary embodiment, the extension 50 includes at least one slot 52, but can include any number of slots 52, including two sets of slots 52 opposing each other, as best seen in FIG. 2. The slots 52 are configured and dimensioned to receive pins 20 and are oriented in an oblique fashion. In another embodiment, the slots 52 may be oriented in a generally vertical orientation.

Figure 12:
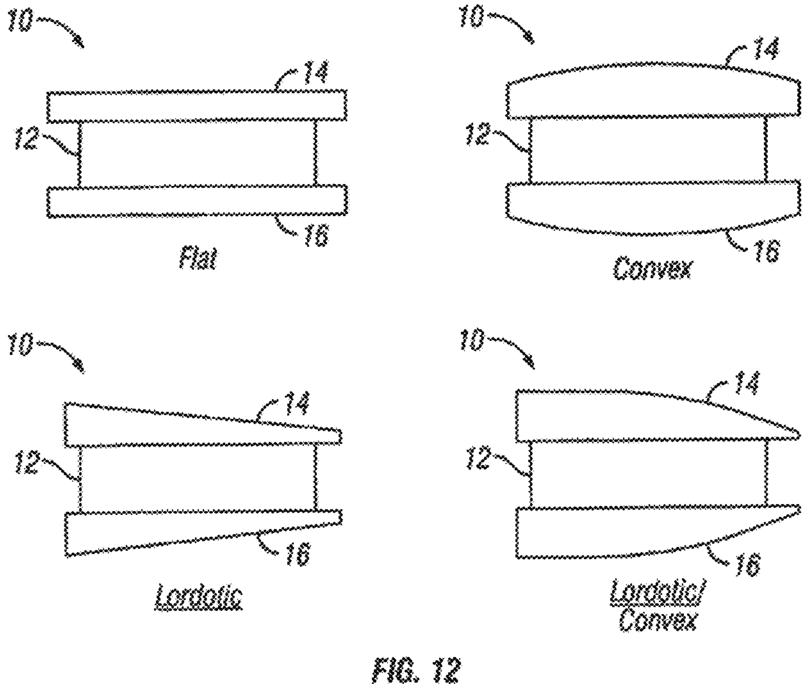
FIG. 12 is a side schematic view of the expandable fusion device of FIG. 1 having different endplates.
Figure 11:
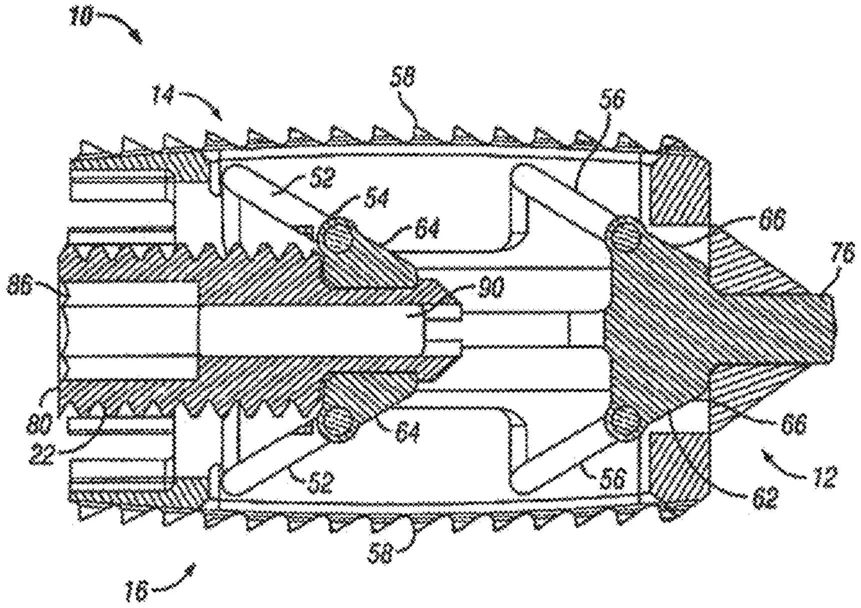
FIG. 11 is a side partial cross-sectional view of the expandable fusion device of FIG. 1 shown in an expanded position.

In an exemplary embodiment, the extension 50 is sized to be received within the central opening 42 of the body portion 12. As best seen in FIGS. 11-12, the lower surface 48 of the first endplate 14 further includes, in an exemplary embodiment, at least one ramped surface 54. In another exemplary embodiment, there are two spaced ramped surfaces 54, 56. It is contemplated that the slope of the ramped surfaces 54, 56 can be equal or can differ from each other. The effect of varying the slopes of the ramped surfaces 54, 56 is discussed below.

Referring now to FIGS. 2-9, in one embodiment, the upper surface 46 of the first endplate 14 is flat and generally planar to allow the upper surface 46 of the endplate 14 to engage with the adjacent vertebral body 2. Alternatively, as shown in FIG. 12, the upper surface 46 can be curved convexly or concavely to allow for a greater or lesser degree of engagement with the adjacent vertebral body 2. It is also contemplated that the upper surface 46 can be generally planar but includes a generally straight ramped surface or a curved ramped surface. The ramped surface allows for engagement with the adjacent vertebral body 2 in a lordotic fashion. Turning back to FIGS. 2-9, in an exemplary embodiment, the upper surface 46 includes texturing 58 to aid in gripping the adjacent vertebral bodies. Although not limited to the following, the texturing can include teeth, ridges, friction increasing elements, keels, or gripping or purchasing projections.

Figure 10:
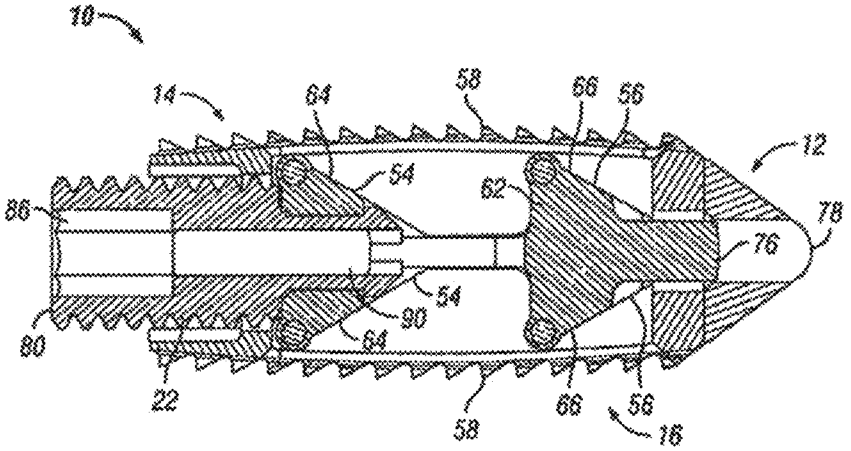
FIG. 10. is a side partial cross-sectional view of the expandable fusion device of FIG. 1 shown in an unexpanded position.

With reference to FIGS. 2 and 10-11, in an exemplary embodiment, the translation member 18 is sized to be received within the central opening 42 of the body portion 12 and includes at least a first expansion portion 60. In another embodiment, the translation member 18 includes a first expansion portion 60 and a second expansion portion 62, the expansion portions 60, 62 being connected together via a bridge portion 68. It is also contemplated that there may be more than two expansion portions where each of the expansion portions is connected by a bridge portion. The expansion portions 60, 62 each have angled surfaces 64, 66 configured and dimensioned to engage the ramp surfaces 54, 56 of the first and second endplates 14, 16. In an exemplary embodiment, the translation member 18 also includes recesses 70, 72, the recesses 70, 72 are sized to receive and retain pins 20. In one embodiment, the expansion portion 60 includes an opening 74, which is sized to receive a portion of the actuation member 22, and the expansion portion 62 includes a nose 76, which is received within an opening 78 in the first end 26 to stabilize the translation member 18 in the central opening 42 of the body member 12.

In an exemplary embodiment, the actuation member 22 has a first end 80, a second end 82 and threading 84 extending along at least a portion thereof from the first end 80 to the second end 82. The threading 84 threadingly engages the threading extending along a portion of opening 40 in the body portion 12. In another exemplary embodiment, the actuation member 22 includes ratchet teeth instead of threading. The ratchet teeth engage corresponding ratchet teeth in the opening 40 in the body portion 12. The first end 80 includes a recess 86 dimensioned to receive an instrument (not shown) that is capable of advancing the actuation member 22 with respect to the body portion 12 of the fusion device 10. The second end 82 of the actuation member 22 includes an extension 88 that is received within the opening 74 of the expansion portion 60. In one embodiment, the extension 88 may include a plurality of slits and a lip portion. The plurality of slits allows the extension portion 88 to flex inwardly reducing its diameter when received in the opening 74. Once the lip portion of the extension portion 88 is advanced beyond the end of the opening 74, the extension portion 88 will return back to its original diameter and the lip portion will engage the expansion portion 60. It is further contemplated that a pin member 90 can be included to prevent the extension portion from flexing inwardly thereby preventing the actuation member 22 from disengaging from the translation member 18.

In an exemplary embodiment, the fusion device 10 can further include a locking mechanism 24. The mechanism 24 is designed to resist rotation of the actuation member 22 rather than prevent rotation of the actuation member 22. In an exemplary embodiment, either deformable threading can be included on actuation member 22 or a disruption of the threading may be included where a deformable material is included in the threading disruption. It is contemplated that the deformable member or deformable threading can be made from a deformable or elastic, biocompatible material such as nitinol or PEEK.

Turning now to FIGS. 1-8 and 10-11, an example method of installing the expandable fusion device 10 is now discussed. Prior to insertion of the fusion device 10, the intervertebral space is prepared. In one method of installation, a diskectomy is performed where the intervertebral disc, in its entirety, is removed. Alternatively, only a portion of the intervertebral disc can be removed. The endplates of the adjacent vertebral bodies 2, 3 are then scraped to create an exposed end surface for facilitating bone growth across the intervertebral space. The expandable fusion device 10 is then introduced into the intervertebral space, with the first end 26 being inserted first into the disc space followed by the second end 28. In an exemplary method, the fusion device 10 is in the unexpanded position when introduced into the intervertebral space. The wedged shaped first end 26 will assist in distracting the adjacent vertebral bodies 2, 3 if necessary. This allows for the option of having little to no distraction of the intervertebral space prior to the insertion of the fusion device 10. In another exemplary method, the intervertebral space may be distracted prior to insertion of the fusion device 10. The distraction provide some benefits by providing greater access to the surgical site making removal of the intervertebral disc easier and making scraping of the endplates of the vertebral bodies 2, 3 easier.

With the fusion device 10 inserted into and seated in the appropriate position in the intervertebral disc space, the fusion device can then expanded into the expanded position, as best seen in FIGS. 1, 4, 6, 8, and 11. To expand the fusion device 10, an instrument is engaged with recess 86 in the actuation member 22. The instrument is used to rotate actuation member 22. As discussed above, actuation member 22 is threadingly engaged body portion 12 and is engaged with translation member 18; thus, as the actuation member 22 is rotated in a first direction, the actuation member 22 and the translation member 18 move with respect to the body portion 12 toward the first end 26 of the body portion 12. In another exemplary embodiment, the actuation member 22 is moved in a linear direction with the ratchet teeth engaging as means for controlling the movement of the actuation member 22 and the translation member 18. As the translation member 18 moves, the ramped surface 64, 66 of the expansion portions 60, 62 push against the ramped surfaces 54, 56 of the endplates 14, 16 pushing endplates 14, 16 outwardly into the expanded position. This can best be seen in FIGS. 10 and 11. Since the expansion of the fusion device 10 is actuated by a rotational input, the expansion of the fusion device 10 is infinite. In other words, the endplates 14, 16 can be expanded to an infinite number of heights dependent on the rotational advancement of the actuation member 22. As discussed above, the fusion device 10 includes a locking mechanism 24 which assists in retaining the endplates 14, 16 at the desired height.

Figure 13:
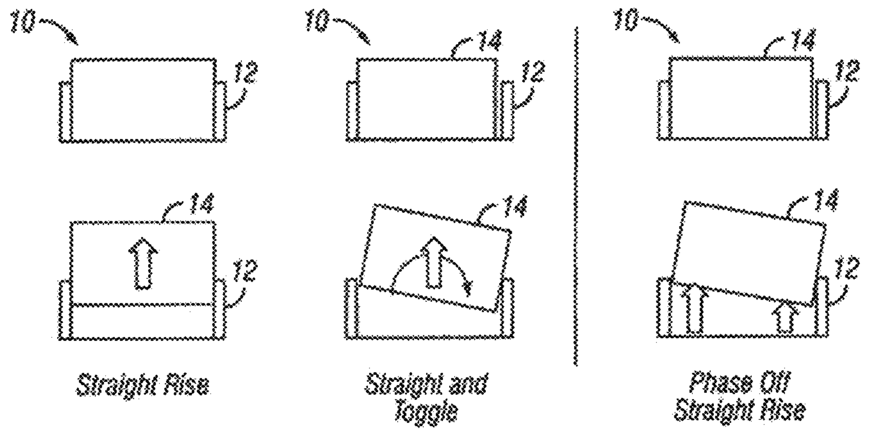
FIG. 13 is a partial side schematic view of the expandable fusion device of FIG. 1 showing different modes of endplate expansion.

It should also be noted that the expansion of the endplates 14, 16 can be varied based on the differences in the dimensions of the ramped surfaces 54, 56, 64, 66. As best seen in FIG. 13, the endplates 14, 16 can be expanded in any of the following ways: straight rise expansion, straight rise expansion followed by a toggle into a lordotic expanded configuration, or a phase off straight rise into a lordotic expanded configuration.

Turning back to FIGS. 1-8 and 10-11, in the event the fusion device 10 needs to be repositioned or revised after being installed and expanded, the fusion device 10 can be contracted back to the unexpanded configuration, repositioned, and expanded again once the desired positioning is achieved. To contract the fusion device 10, the instrument is engaged with recess 86 in the actuation member 22. The instrument is used to rotate actuation member 22. As discussed above, actuation member 22 is threadingly engaged body portion 12 and is engaged with translation member 18; thus, as the actuation member 22 is rotated in a second direction, opposite the first direction, the actuation member 22 and translation member 18 move with respect to the body portion 12 toward the second end 28 of the body portion 12. As the translation member 18 moves, the pins 20, a portion of which are located within the slots 52, ride along the slots 52 pulling the endplates 14, 16 inwardly into the unexpanded position.

Figure 14:
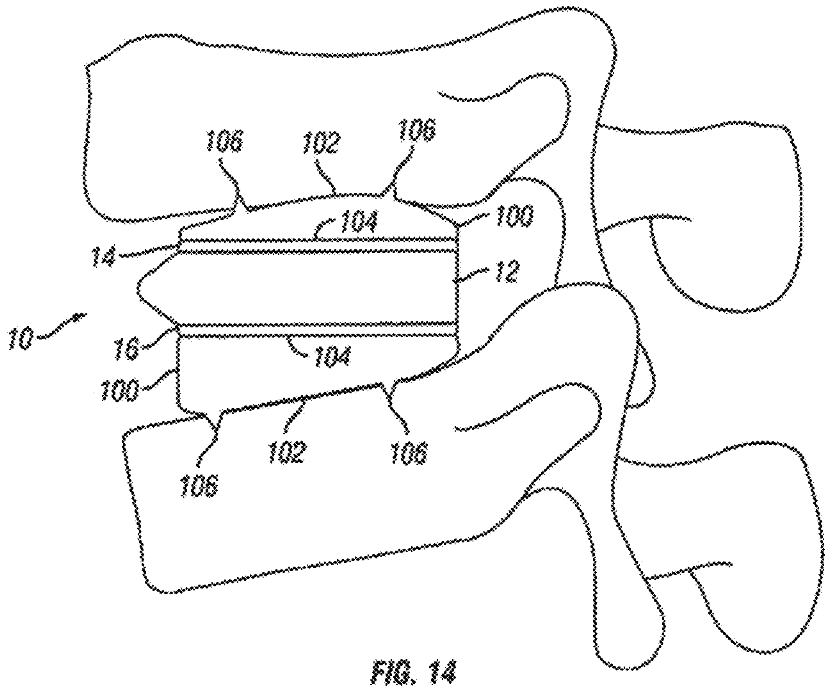
FIG. 14 is a side schematic view of the expandable fusion device of FIG. 1 with artificial endplates shown between adjacent vertebrae.

With reference now to FIG. 14, fusion device 10 is shown with an exemplary embodiment of artificial endplates 100. Artificial endplates 100 allows the introduction of lordosis even when the endplates 14 and 16 of the fusion device 10 are generally planar. In one embodiment, the artificial endplates 100 have an upper surface 102 and a lower surface 104. The upper surfaces 102 of the artificial endplates 100 have at least one spike 106 to engage the adjacent vertebral bodies. The lower surfaces 104 have complementary texturing or engagement features on their surfaces to engage with the texturing or engagement features on the upper endplate 14 and the lower endplate 16 of the fusion device 10. In an exemplary embodiment, the upper surface 102 of the artificial endplates 100 have a generally convex profile and the lower surfaces 104 have a generally parallel profile to achieve lordosis. In another exemplary embodiment, fusion device 10 can be used with only one artificial endplate 100 to introduce lordosis even when the endplates 14 and 16 of the fusion device 10 are generally planar. The artificial endplate 100 can either engage endplate 14 or engage endplate 16 and function in the same manner as described above with respect to two artificial endplates 100.

Figure 15:
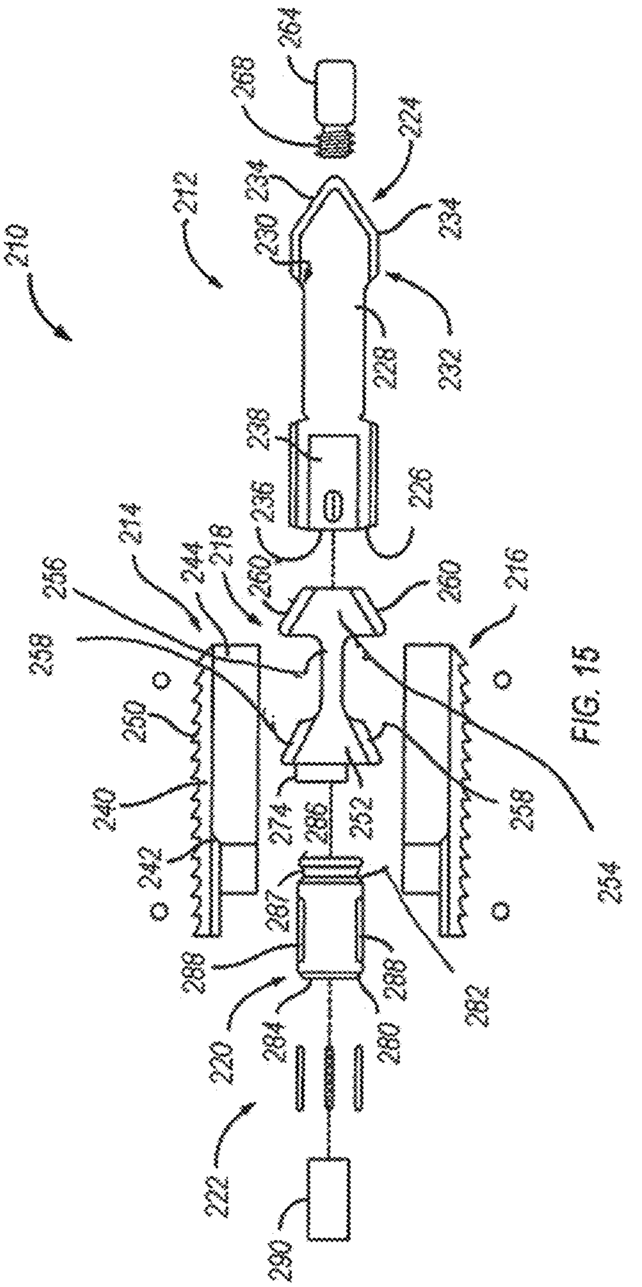
FIG. 15 is an exploded view of an alternative embodiment of an expandable fusion according to the present invention.

With reference to FIG. 15, an exploded perspective view of alternative embodiment of a fusion device 210 is shown. In an exemplary embodiment, the fusion device 210 includes a body portion 212, a first endplate 214, a second endplate 216, a translation member 218, an actuation member 220, and an insert 222.

With additional reference to FIGS. 16-19, in an exemplary embodiment, the body portion 212 has a first end 224, a second end 226, a first side portion 228 connecting the first end 224 and the second end 226, and a second side portion 229 on the opposing side of the body portion 212 connecting the first end 224 and the second end 226. The body portion 212 further includes an upper end 230, which is sized to receive at least a portion of the first endplate 214, and a lower end 232, which is sized to receive at least a portion of the second endplate 216.

The first end 224 of the body portion 212, in an exemplary embodiment, includes at least one angled surface 234, but can include multiple angled surfaces. The angled surface 234 can serve to distract the adjacent vertebral bodies when the fusion device 210 is inserted into an intervertebral space. In another preferred embodiment, it is contemplated that there are at least two opposing angled surfaces forming a generally wedge shaped to distract the adjacent vertebral bodies when the fusion device 210 is inserted into an intervertebral space.

The second end 226 of the body portion 212, in an exemplary embodiment, includes an opening 236 which may include threading. In another exemplary embodiment, the opening 236 may include ratchet teeth instead of threading. The opening 236 extends from the second end 226 of the body portion 212 into a central opening (not illustrated) in the body portion 212. In one embodiment, the central opening is sized to receive the translation member 218, and the opening 236 is sized to threadingly receive the actuation member 220. In another exemplary embodiment, the opening 236 is sized to receive the actuation member 220 in a ratcheting fashion. In yet another exemplary embodiment, first side portion 228 and second side portion 229 each include a recess 238 located towards the second end 226 of the body portion 212. The recess 238 is configured and dimensioned to receive an insertion instrument (not shown) that assists in the insertion of the fusion device 210 into an intervertebral space.

Although the following discussion relates to the first endplate 214, it should be understood that it also equally applies to the second endplate 216 as the second endplate 216 is substantially identical to the first endplate 214 in embodiments of the present invention. Turning now to FIGS. 15-19, in an exemplary embodiment, the first endplate 214 has an upper surface 240, a lower surface 242, and a through opening 243. The through opening 243, in an exemplary embodiment, is sized to receive bone graft or similar bone growth inducing material and further allow the bone graft or similar bone growth inducing material to be packed in the central opening in the body portion 212.

Figure 16:
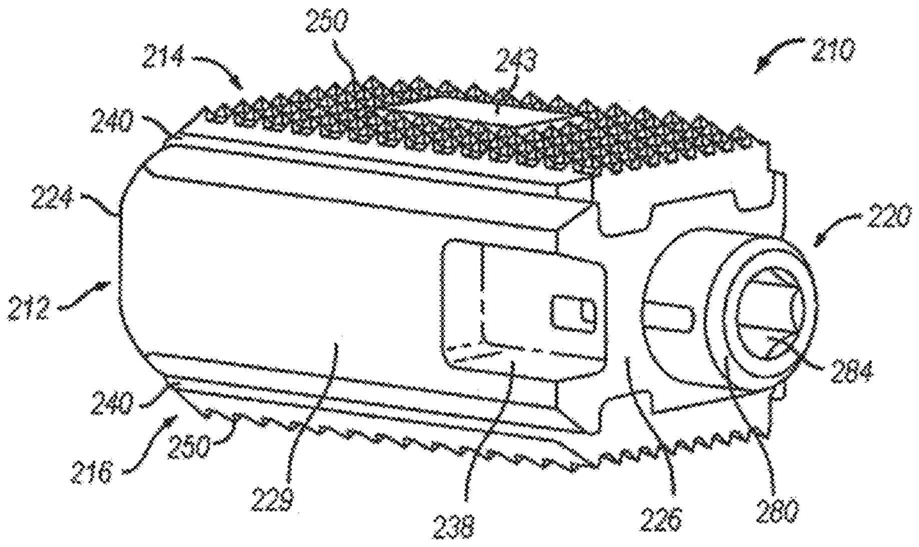
FIG. 16 is a rear perspective view of the expandable fusion device of FIG. 15 shown in an unexpanded position.
Figure 17:
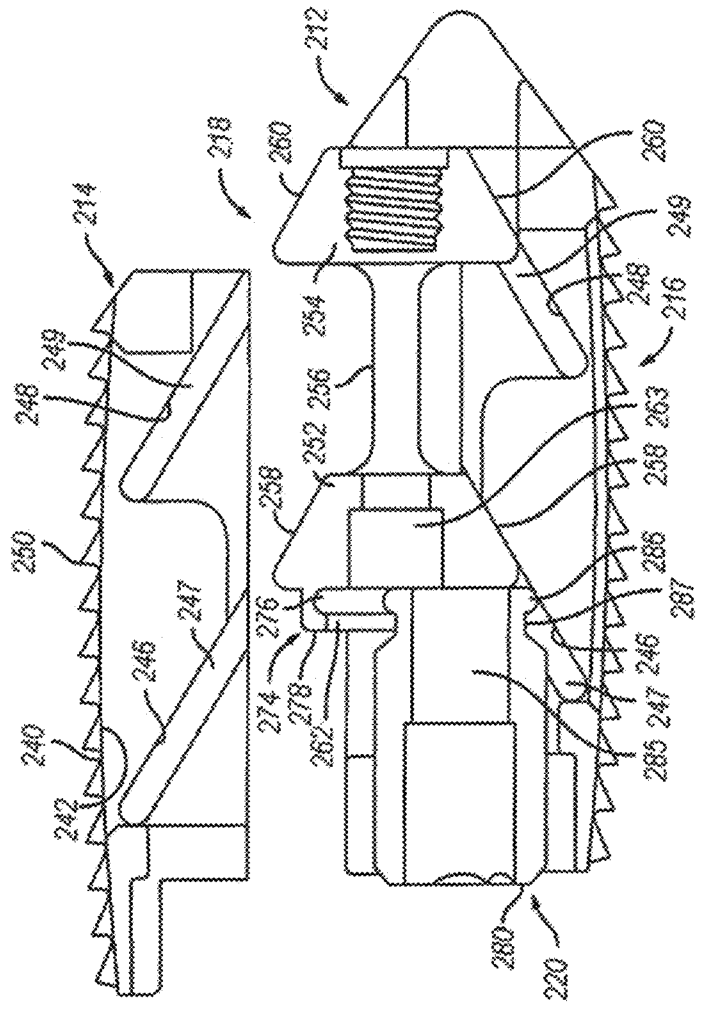
FIG. 17 is a side cross-sectional view of the expandable fusion device of FIG. 15 shown with one of the endplates removed.

In one embodiment, the lower surface 242 includes at least one extension 244 extending along at least a portion of the lower surface 242. As best seen in FIGS. 16 and 17, in an exemplary embodiment, the extension 244 can extend along a substantial portion of the lower surface 242, including, along each side of the endplate 214 and along the front end of the endplate 214. In another exemplary embodiment, the extension 244 includes at least one ramped portion 246, but can include any number of ramped portions, including two spaced ramped portions 246, 248 in the extension 244 that extend between each side of the endplate 214, as best seen in FIG. 17. It is contemplated that the slope of the ramped portions 246, 248 can be equal or can differ from each other. The effect of varying the slopes of the ramped portions 246, 248 is discussed below.

In an exemplary embodiment, the ramped portions 246, 248 further include grooved portions 247, 249 that are configured and dimensioned to receive angled surfaces 258, 260 of the translation member 218 and are oriented in an oblique fashion. In a preferred embodiment, the grooved portions 246, 248 are dovetail grooves configured and dimensioned to hold the angled surfaces 258, 260 of the translation member 218 while allowing the angles surfaces 258, 260 to slide against the ramped portions 246, 248.

Figure 1:
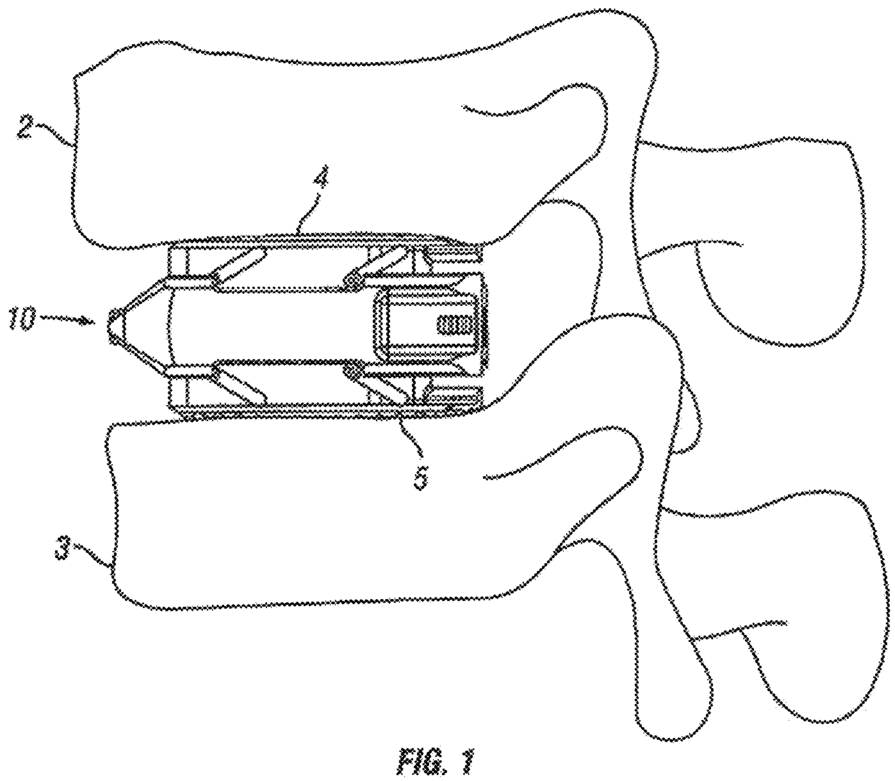
FIG. 1 is a side view of an embodiment of an expandable fusion device shown between adjacent vertebrae according to the present invention.

Referring now to FIGS. 16-19, in one embodiment, the upper surface 240 of the first endplate 214 is flat and generally planar to allow the upper surface 240 of the endplate 214 to engage with the adjacent vertebral body 2 (e.g., shown on FIG. 1). Alternatively, as shown in the upper surface 240 can be curved convexly or concavely to allow for a greater or lesser degree of engagement with the adjacent vertebral body 2, as shown on FIG. 12 with respect to fusion device 10, for example. It is also contemplated that the upper surface 240 can be generally planar but includes a generally straight ramped surface or a curved ramped surface. The ramped surface allows for engagement with the adjacent vertebral body 2 in a lordotic fashion. Turning back to FIGS. 15-19, in an exemplary embodiment, the upper surface 240 includes texturing 250 to aid in gripping the adjacent vertebral bodies. Although not limited to the following, the texturing can include teeth, ridges, friction increasing elements, keels, or gripping or purchasing projections.

Figure 18:
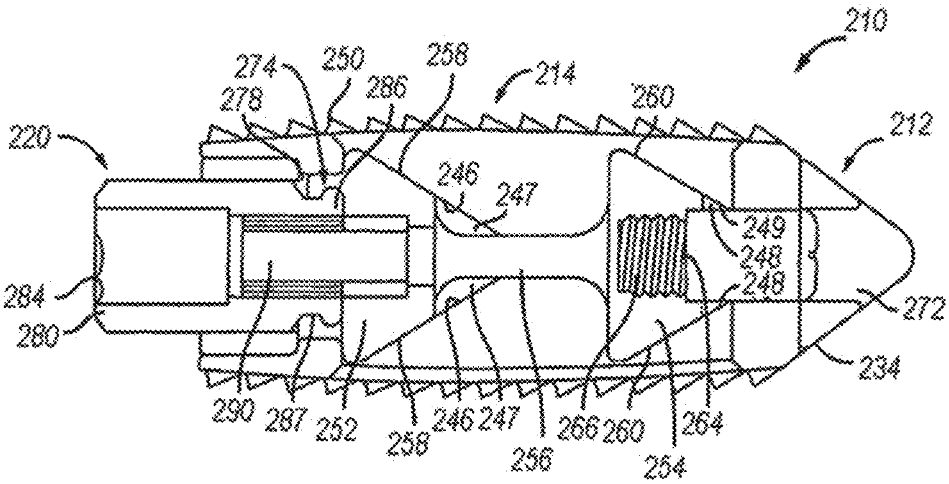
FIG. 18 is a side partial cross-sectional view of the expandable fusion device of FIG. 15 shown in an unexpanded position.
Figure 19:
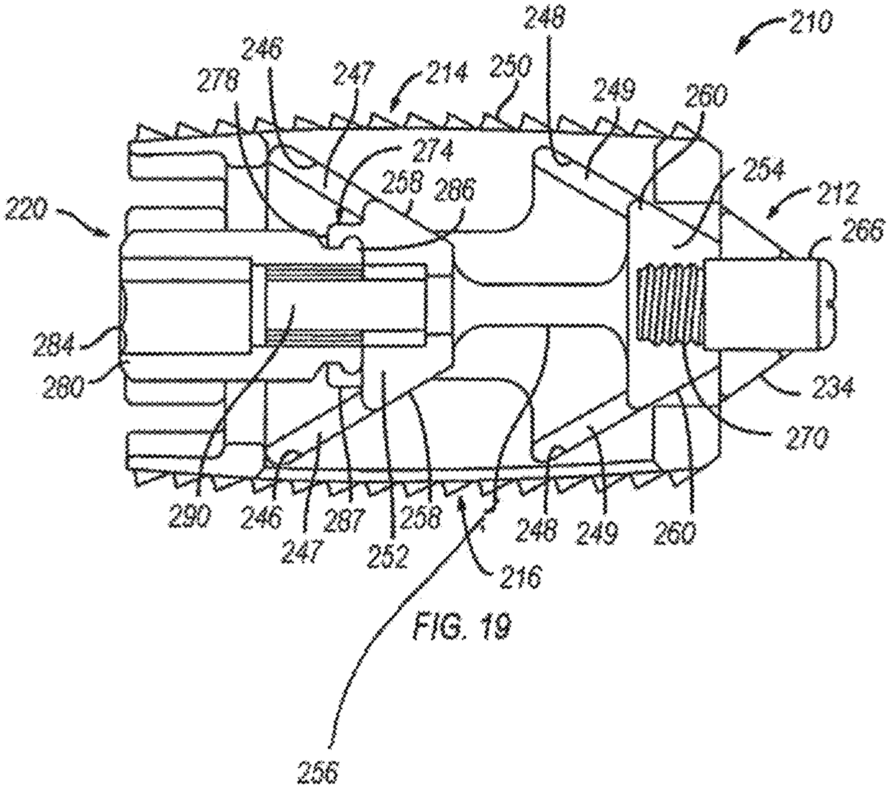
FIG. 19 is a side partial cross-sectional view of the expandable fusion device of FIG. 15 shown in an expanded position.

With reference to FIGS. 15 and 17-19, in an exemplary embodiment, the translation member 218 is sized to be received within the central opening of the body portion 212 and includes at least a first expansion portion 252. In another embodiment, the translation member 218 includes a first expansion portion 252 and a second expansion portion 254, the expansion portions 252, 254 being connected together via a bridge portion 256. It is also contemplated that there may be more than two expansion portions where each of the expansion portions is connected by a bridge portion. The expansion portions 252, 254 each have angled surfaces 258, 260 configured and dimensioned to engage the grooved portions 246, 248 of the first and second endplates 214, 216. In one embodiment, the translation member 218 includes an opening 262 in the first expansion portion 252, which is sized to receive a portion of the actuation member 220, as best seen in FIG. 17. In an exemplary embodiment, the first expansion portion 252 includes a central bore 263 that extends from the opening 262 and through the first expansion portion 252. In one embodiment, the translation member 218 includes a hole 264 in the second expansion portion 254, which is sized to receive nose 266, as best seen in FIGS. 18 and 19. In an exemplary embodiment, the hole 264 includes threading 268 for threadedly receiving a threaded end 270 of the nose 266, as shown on FIG. 19. The nose 266 is received in an opening 272 in the first end 234 of the body portion 212 to stabilize the translation member 218 in the central opening of the body portion 212.

In one embodiment, the translation member 218 includes a locking mechanism 274, which is configured and adapted to engage the actuation member 220. As illustrated, the locking mechanism 274 may extend from the first expansion portion 252. The locking mechanism 274 includes a slot 276 configured and adapted to receive extension 287 of the actuation member 220. In an exemplary embodiment, the locking mechanism 274 further includes a stop 278 (e.g., a rim, a lip, etc.) that engages the actuation member 220 when it is disposed in the slot 276.

Referring now to FIGS. 15-19, in an exemplary embodiment, the actuation member 220 has a first end 280, a second end 282, and threading (not illustrated) extending along at least a portion thereof from the first end 280 to the second end 282. The threading threadingly engages the threading that extends along a portion of opening 236 in the body portion 212. In another exemplary embodiment, the actuation member 220 includes ratchet teeth instead of threading. The ratchet teeth engage corresponding ratchet teeth in the opening 236 in the body portion 212. The first end 280 includes a recess 284 dimensioned to receive an instrument (not shown) that is capable of advancing the actuation member 220 with respect to the body portion 212 of the fusion device 210. In an embodiment, the actuation member 220 includes a bore 285, as best seen by FIG. 17, that extends from the recess 284 in the first end to the second 282. The second end 282 of the actuation member 220 includes an extension 286 that is received within the opening 262 in the first expansion portion 252. In one embodiment, the extension 288 may include a lip portion 286 and a plurality of slits 288. The plurality of slits 288 are configured to receive inserts 222. Inserts 222 are provided to limit motion of the actuation member 220. Once the lip portion 286 is placed into the slot 276 of the locking mechanism 274, the lip portion 286 will engage the stop 278 preventing longitudinal movement of the actuation member 220 with respect to the translation member 218. It is further contemplated that a pin member 290 can be included to further secure the actuation member 220 in the translation member 218. In an embodiment, the pin member 290 can be pressed into the central bore 285 of the actuation member 220 and the central bore 263 of the translation member, thereby preventing the actuation member 220 from disengaging from the translation member 218. Additionally, in an exemplary embodiment, the fusion device 210 can further include a chamfered tip 224 for distraction of adjacent vertebrae.

Turning now to FIGS. 2-19, an example method of installing the expandable fusion device 210 is now discussed. Prior to insertion of the fusion device 210, the intervertebral space is prepared. In one method of installation, a diskectomy is performed where the intervertebral disc, in its entirety, is removed. Alternatively, only a portion of the intervertebral disc can be removed. The endplates of the adjacent vertebral bodies 2, 3 (shown on FIG. 1, for example) are then scraped to create an exposed end surface for facilitating bone growth across the intervertebral space. The expandable fusion device 210 is then introduced into the intervertebral space, with the first end 222 of the body portion 212 being inserted first into the disc space followed by the second end 224. In an exemplary method, the fusion device 210 is in the unexpanded position when introduced into the intervertebral space. The wedged-shaped first end 222 should assist in distracting the adjacent vertebral bodies 2, 3, if necessary. This allows for the option of having little to no distraction of the intervertebral space prior to the insertion of the fusion device 210. In another exemplary method, the intervertebral space may be distracted prior to insertion of the fusion device 210. The distraction provide some benefits by providing greater access to the surgical site making removal of the intervertebral disc easier and making scraping of the endplates of the vertebral bodies 2, 3 easier.

With the fusion device 210 inserted into and seated in the appropriate position in the intervertebral disc space, the fusion device can then expanded into the expanded position, as best seen in FIGS. 18 and 19, to expand the fusion device 210, an instrument is engaged with recess 284 in the actuation member 220. The instrument is used to rotate actuation member 220. As discussed above, actuation member 220 can be threadingly engaging body portion 212 and is engaged with translation member 218; thus, as the actuation member 220 is rotated in a first direction, the actuation member 220 and the translation member 218 move with respect to the body portion 212 toward the first end 222 of the body portion 212. In another exemplary embodiment, the actuation member 220 is moved in a linear direction with the ratchet teeth engaging as means for controlling the movement of the actuation member 220 and the translation member 218. As the translation member 218 moves, the angled surfaces 258, 260 of the expansion portions 252, 254 push against the ramped portions 246, 248 of the endplates 214, 216 pushing endplates 214, 216 outwardly into the expanded position with the angled surfaces 258, 260 riding along the grooved portions 247, 248 of the ramped portions 246, 248. This can best be seen in FIGS. 18 and 19. Since the expansion of the fusion device 210 is actuated by a rotational input, the expansion of the fusion device 210 is infinite. In other words, the endplates 214, 216 can be expanded to an infinite number of heights dependent on the rotational advancement of the actuation member 220. As discussed above, the fusion device 210 includes a locking mechanism 222 which assists in retaining the endplates 214, 216 at the desired height.

It should also be noted that the expansion of the endplates 214,216 can be varied based on the differences in the dimensions of the ramped portions 246, 248 and the angled surfaces 258, 260. For example, the endplates 214, 216 can be expanded in any of the following ways: straight rise expansion, straight rise expansion followed by a toggle into a lordotic expanded configuration, or a phase off straight rise into a lordotic expanded configuration, which are discussed above with respect to FIG. 13 for fusion device 10.

Turning back to FIGS. 15-19, in the event the fusion device 210 needs to be repositioned or revised after being installed and expanded, the fusion device 210 can be contracted back to the unexpanded configuration, repositioned, and expanded again once the desired positioning is achieved. To contract the fusion device 210, the instrument is engaged with recess 284 in the actuation member 220. The instrument is used to rotate actuation member 220. As discussed above, actuation member 220 can be threadingly engaging body portion 212 and is engaged with translation member 218; thus, as the actuation member 220 is rotated in a second direction, opposite the first direction, the actuation member 220 and translation member 218 move with respect to the body portion 212 toward the second end 226 of the body portion 212. As the translation member 218 moves, the angled surfaces 258, 260 of the translation member 218 ride along the grooved portions 247, 249 pulling the endplates 214,216 inwardly into the unexpanded position.

In some embodiments, artificial endplates (e.g., endplates 100 shown on FIG. 14) may be used with fusion device 210. As will be appreciated, the artificial endplates allow the introduction of lordosis even when the endplates 214 and 216 of the fusion device 210 are generally planar.

Figure 20:
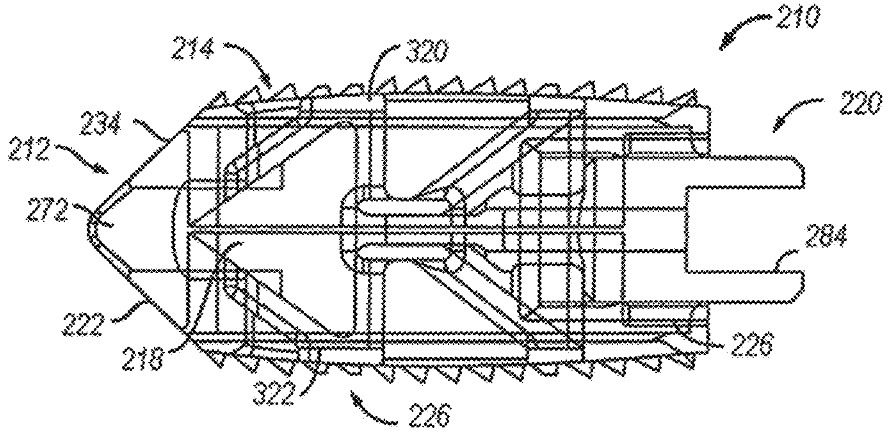
FIG. 20 is a side view cross-sectional view of another embodiment of an expandable fusion device shown in an unexpanded position.
Figure 21:
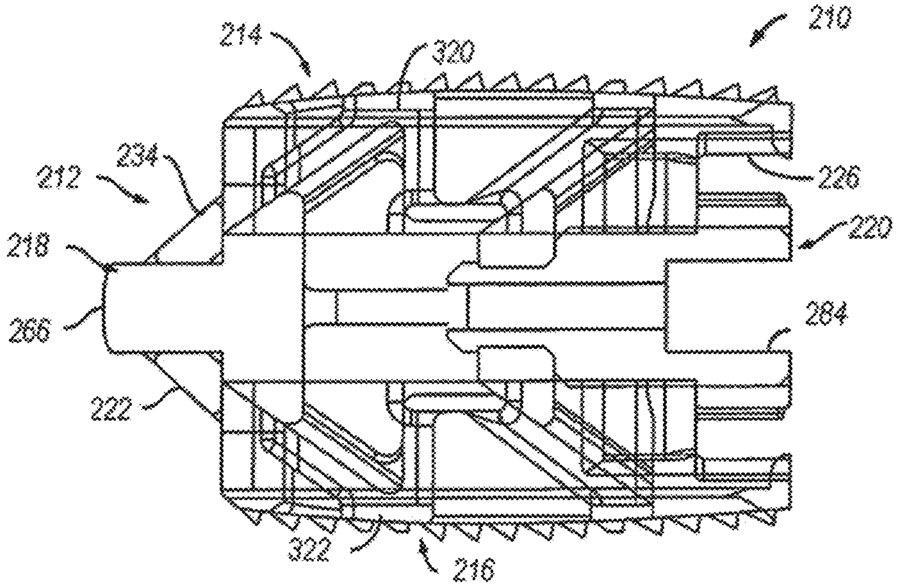
FIG. 21 is a side view cross-sectional view of the expandable fusion device of FIG. 20 shown in an expanded position.
Figure 22:
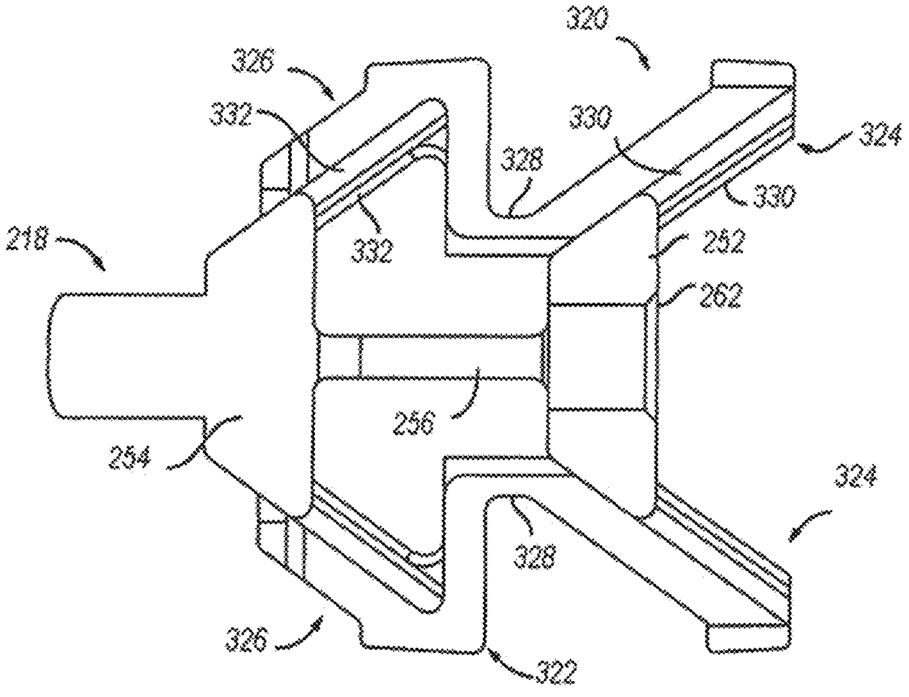
FIG. 22 is a side view of the expandable fusion device of FIG. 20 showing the translation member and the ramped insert.
Figure 23:
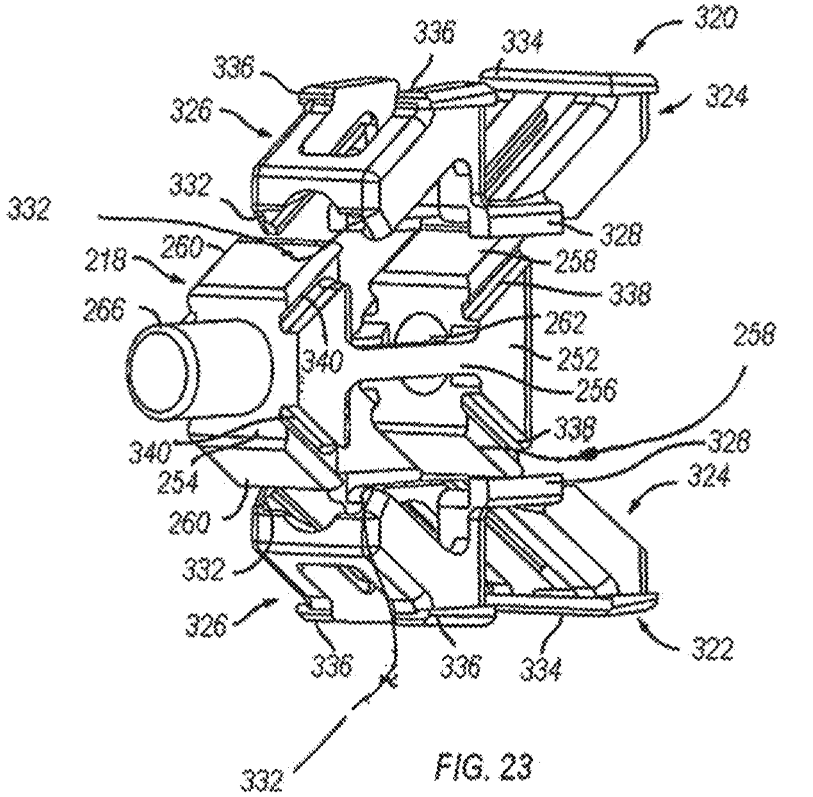
FIG. 23 is a front perspective view of the expandable fusion device of FIG. 20 showing the translation member and the ramped insert.

Referring now to FIGS. 20 and 21, an alternative embodiment of the fusion device 210 is shown. In an exemplary embodiment, the fusion device 210 includes a body portion 212, a first endplate 214, a second endplate 216, a translation member 218, and an actuation member 220. In the illustrated embodiment, the fusion device further includes a first ramped insert 320 and a second ramped insert 322.

Although the following discussion relates to the first ramped insert 320, it should be understood that it also equally applies to the second ramped insert 322 as the second ramped insert 322 is substantially identical to the first ramped insert 320 in embodiments of the present invention. Turning now to FIGS. 20-23, in an exemplary embodiment, the first ramped insert 320 includes a first ramped portion 324 and a second ramped portion 326, the first and second ramped portions 324, 326 being connected by a bridge portion 328. The ramped portions 324, 326 each have grooved portions 330, 332 configured and dimensioned to receive angled surfaces 258, 260 of the translation member. The ramped portions 324, 326 can be oriented in an oblique fashion, as illustrated. In a preferred embodiment, the grooved portions 330, 332 are dovetail grooves configured and dimensioned to hold the angled surfaces 258, 260 of the translation member 218 while allowing the angles surfaces 258, 260 to slide against the ramped portions 324, 326.

In an exemplary embodiment, the first ramped insert 320 should be configured and dimensioned to be engaged with the first endplate 214. In an embodiment, the first and second ramped portions 324, 326 include snap connectors 334, 336 for securing the first ramped insert 320 to the first endplate. It should be understood that the snap connectors 334, 336 are merely illustrative and that other suitable mechanisms for securing the first ramped inserted 320 with the first endplate 214 may be used.

Referring to FIGS. 20-23, in an exemplary embodiment, the translation member 218 is sized to be received within the central opening of the body portion 212 and includes at least a first expansion portion 252. In another embodiment, the translation member 218 includes a first expansion portion 252 and a second expansion portion 254, the expansion portions 252, 254 being connected together via a bridge portion 256. It is also contemplated that there may be more than two expansion portions where each of the expansion portions is connected by a bridge portion. The expansion portions 252, 254 each have angled surfaces 258, 260 configured and dimensioned to engage the grooved portions 330, 332 of the first and second ramped inserts 320, 322. In one embodiment, the angled surfaces 258, 260 include corresponding grooved portions 338, 340, as best seen in FIG. 13, that slidingly engaged the grooved portions 330, 332 of the first and second ramped inserts 320, 322.

In one embodiment, the expansion portion 252 includes an opening 262, which is sized to receive a portion of the actuation member 220, and the expansion portion 262 includes a nose 266, which is received within an opening 272 in the first end 234 of the body portion 212 to stabilize the translation member 218 in the central opening of the body portion 212. In an embodiment, the nose 266 is integral with the expansion portion 262. In an embodiment (shown on FIGS. 15 and 17-19), the nose 266 is threadingly engaged with the expansion portion 262. In an embodiment, the translation member 218 includes a locking mechanism 274 to engage the actuation member 220, as illustrated in FIGS. 15-19. However, it should be understood that other suitable mechanisms may be used to secure the actuation member 220 within the translation member 218. For example, the actuation member 220 may include an extension 287 having a lip portion 286 (shown on FIGS. 15 and 17-19) that engages the expansion portion 262. The extension 287 may, for example, be configured to flex inwardly reducing its diameter when received in the opening 262. Once the lip portion 286 of the extension 287 is advanced beyond the end of the opening 262, the extension portion 287 will return back to its original diameter and the lip portion 286 will engage the expansion portion 260.

The expandable fusion device 210 of FIGS. 20-23 can be inserted into the intervertebral space in a manner similar to that the previously described with respect to FIGS. 15-19. After insertion, the expandable fusion device 210 of FIGS. 20-23 can be expanded into the expanded position, as best seen in FIGS. 20 and 21. To expand the fusion device 210, an instrument is engaged with recess 284 in the actuation member 220. The instrument is used to rotate actuation member 220. As discussed above, actuation member 220 can be threadingly engaging body portion 212 and is engaged with translation member 218; thus, as the actuation member 220 is rotated in a first direction, the actuation member 220 and the translation member 218 move with respect to the body portion 212 toward the first end 222 of the body portion 212. In another exemplary embodiment, the actuation member 220 is moved in a linear direction with the ratchet teeth engaging as means for controlling the movement of the actuation member 220 and the translation member 218. As the translation member 218 moves, the angled surfaces 258, 260 of the expansion portions 252, 254 push against the ramped portions 324, 326 of the first and second ramped inserts 320, 322 while riding along the grooved portions 330, 332, thus pushing first and second ramped inserts 320, 322 outwardly. Because the first and second ramped inserts 320, 322 are engaged with the endplates 214, 216, the endplates 214, 216 are also pushed outwardly into the expanded position.

After expansion, the expandable fusion device 210 can be contracted back to the unexpanded configuration. To contract the fusion device 210, the instrument is engaged with recess 284 in the actuation member 220. The instrument is used to rotate actuation member 220. As discussed above, actuation member 220 can be threadingly engaging body portion 212 and is engaged with translation member 218; thus, as the actuation member 220 is rotated in a second direction, opposite the first direction, the actuation member 220 and translation member 218 move with respect to the body portion 212 toward the second end 226 of the body portion 212. As the translation member 218 moves, the angled surfaces 258, 260 of the translation member 218 ride along the grooved portions 330, 332 pulling the first and second ramped inserts 320,322 and thus, the endplates 214, 216 inwardly into the unexpanded position.

Figure 24:
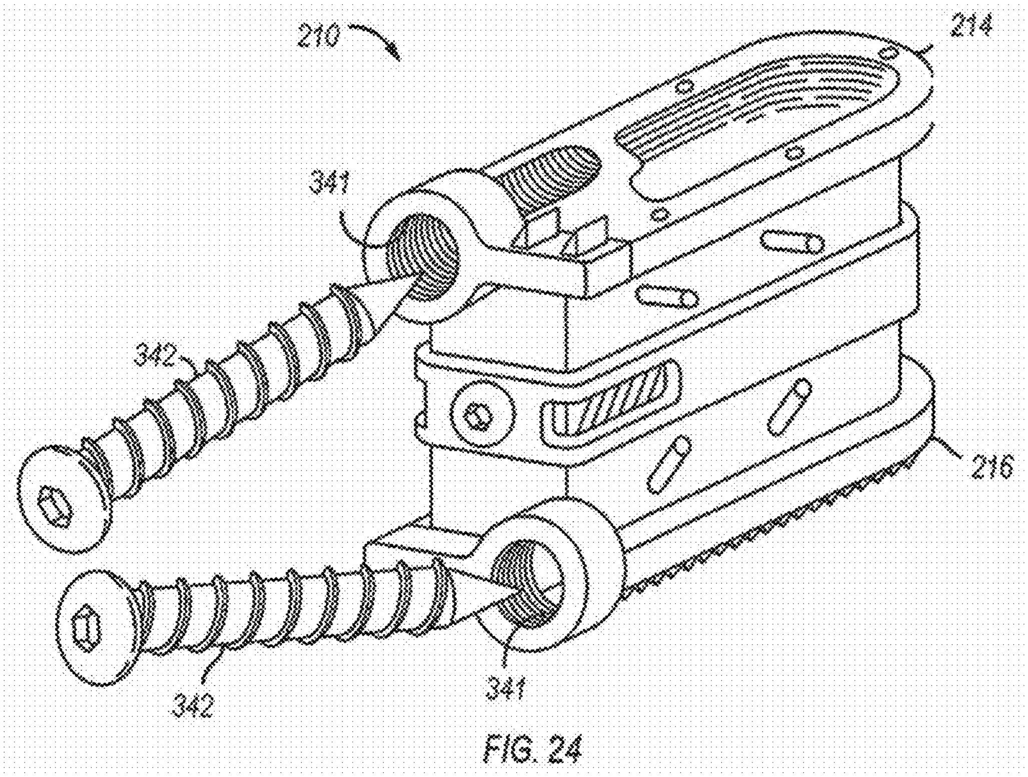
FIG. 24 is a rear perspective of another embodiment of an expandable fusion device with the endplates having a threaded hole.

Referring now to FIG. 24, an alternative embodiment of the fusion device 210 is shown. In an exemplary embodiment, the first endplate 214 and the second endplate 216 each include additional geometry to help securely hold the endplates 214,216 in place. In an embodiment, the first endplate 214 and/or the second endplate 216 include threaded holes 341 through which the fasteners, such as screws 342, may be inserted. In an embodiment, the threaded holes 341 penetrate through the first endplate 214 and/or the second endplate 216 in an oblique fashion. It is contemplated that the screws 342 may inserted through the threaded holes 341 and into adjacent vertebral bodies 2, 3 (shown on FIG. 1, for example), to further secure the first endplate 214 and the second endplate 216 to the vertebral bodies 2, 3. In some embodiments, these fasteners may be removed once a more long-term interface has been established, or alternatively the fasteners may remain in place indefinitely or until the fusion device 210 needs adjustment and/or replacement.

Figure 25:
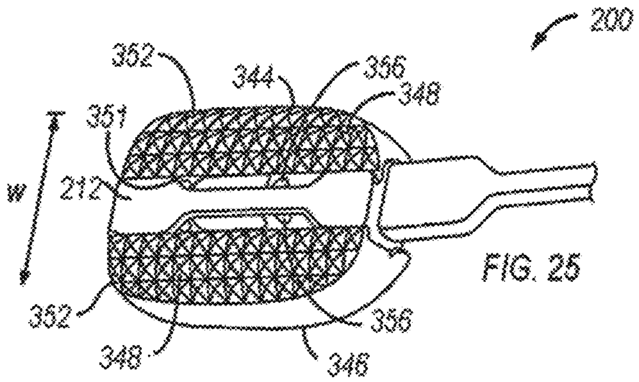
FIG. 25 is a top view of another embodiment of an expandable fusion device shown in an unexpanded position.
Figure 26:
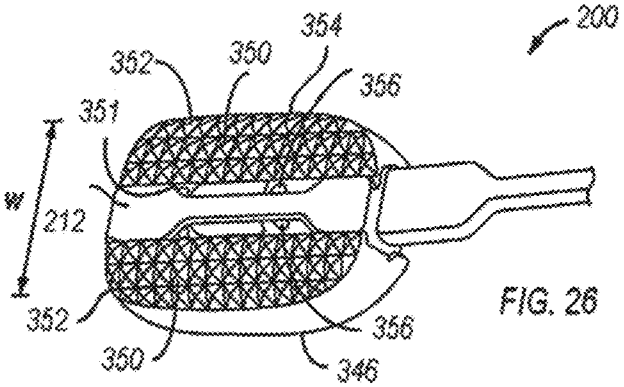
FIG. 26 is a bottom view of the expandable fusion device of FIG. 25.
Figure 27:
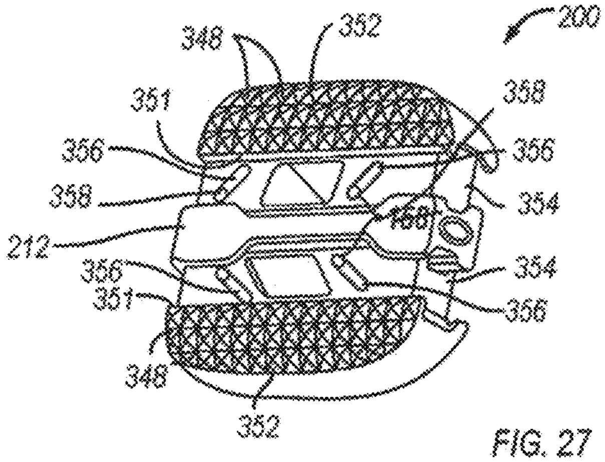
FIG. 27 is top view of the expandable fusion device of FIG. 25 shown in an expanded position.

With reference now FIGS. 25-27, an alternative embodiment of the fusion device 210 is shown that expands laterally. Lateral expansion maximizes coverage of the intervertebral disc space for wider load distribution and stability providing a rigid foundation for fusion. In one embodiment, the fusion device 210 includes body portion 212, first endplate 344, and second endplate 346.

Although the following discussion relates to the first endplate 344, it should be understood that it also equally applies to the second endplate 346 as the second endplate 346 is substantially identical to the first endplate 344 in embodiments of the present invention. Turning now to FIGS. 25-27, in an exemplary embodiment, the first endplate 344 has an upper surface 348, a lower surface 350, and an inner surface 351 facing the body portion 312. It is contemplated that the upper surface 2348 will engage adjacent vertebral body 2 (seen on FIG. 1, for example) and the lower surface 350 will engage adjacent vertebral body 3 (seen on FIG. 1, for example). In one embodiment, the upper surface 348 and the lower surface 350 are each flat and generally planar to allow the upper surface 348 to engage with the adjacent vertebral body 3. Alternatively, the upper surface 348 and/or the lower surface 350 can be curved convexly or concavely to allow for a greater or lesser degree of engagement with the adjacent vertebral bodies 2, 3. It is also contemplated that the upper surface 348 and/or the lower surface 350 can be generally planar but includes a generally straight ramped surface or a curved ramped surface. The ramped surface allows for engagement with the adjacent vertebral body 2 and/or the adjacent vertebral body 3 in a lordotic fashion. In an exemplary embodiment, the upper surface 2348 and/or lower surface 350 includes textures 352 to aid in gripping the adjacent vertebral bodies. Although not limited to the following, the texturing can include teeth, ridges, friction increasing elements, keels, or gripping or purchasing projections.

In one embodiment, the inner surface 351 includes at least one extension 354 extending along at least a portion of the inner surface 351. In an exemplary embodiment, the extension 354 can extend along a substantial portion of the inner surface 354, including, along each side of the endplate 344 and along the front end of the endplate 344. While not illustrated, the inner surface may include ramped surfaces and grooved portions in an exemplary embodiment. It is contemplated that the ramped surfaces and/or grooved portions may be similar to the ramped surfaces 246, 248 and grooved portion 247, 249 in extension 344 shown on FIGS. 17-19. In an embodiment, the extension 354 may include slots 356 oriented in an oblique fashion through which pins 358 may be inserted.

While not illustrated, the fusion device 210 further includes features to effectuate the lateral expansion of the first and second endplates 344, 346. In one embodiment, the fusion device 210 using a ramping system-similar to the system illustrated in FIGS. 15 and 17-19—for expanding the first and second endplates 344, 346. In an exemplary embodiment, the fusion device 210 further includes a translation member and actuation member, such as translation member 218 and actuation member 220 shown on FIGS. 15 and 17-19. It is contemplated that the translation member may include angled surfaces that push against ramped surfaces in the extension 354, expanding the first and second endplates 344, 346 outwardly and away from the body portion 212. In an embodiment, pins 356 disposed through the slots 354 may be retained in the translation member. In an alternative embodiment, dovetailing may be used for engagement of the angled surfaces and ramped surfaces. It should be understood that the translation member and actuation member in this embodiment may be similar to the translation member 218 and actuation member 220 described above with respect FIGS. 15-19. In another embodiment, the fusion device 210 further includes first and second ramped inserts that are secured within the first and second endplates 344, 346. The first and second ramped inserts may be similar to the first and second ramped inserts 320, 322 described above with respect to FIGS. 20-23. It is contemplated that angled surfaces in the translation member may push against ramped surfaces in the ramped inserts pushing the ramped inserts outwardly. Because of their engagement with the first and second endplates 344, 346, the first and second endplates 344, 346 may thus be expanded outwardly. In this manner, the first and second endplates 344, 346 may be laterally expanded away from the body portion 212. It should be understood that other suitable techniques may also be used to effectuate this lateral expansion.

Figure 28:
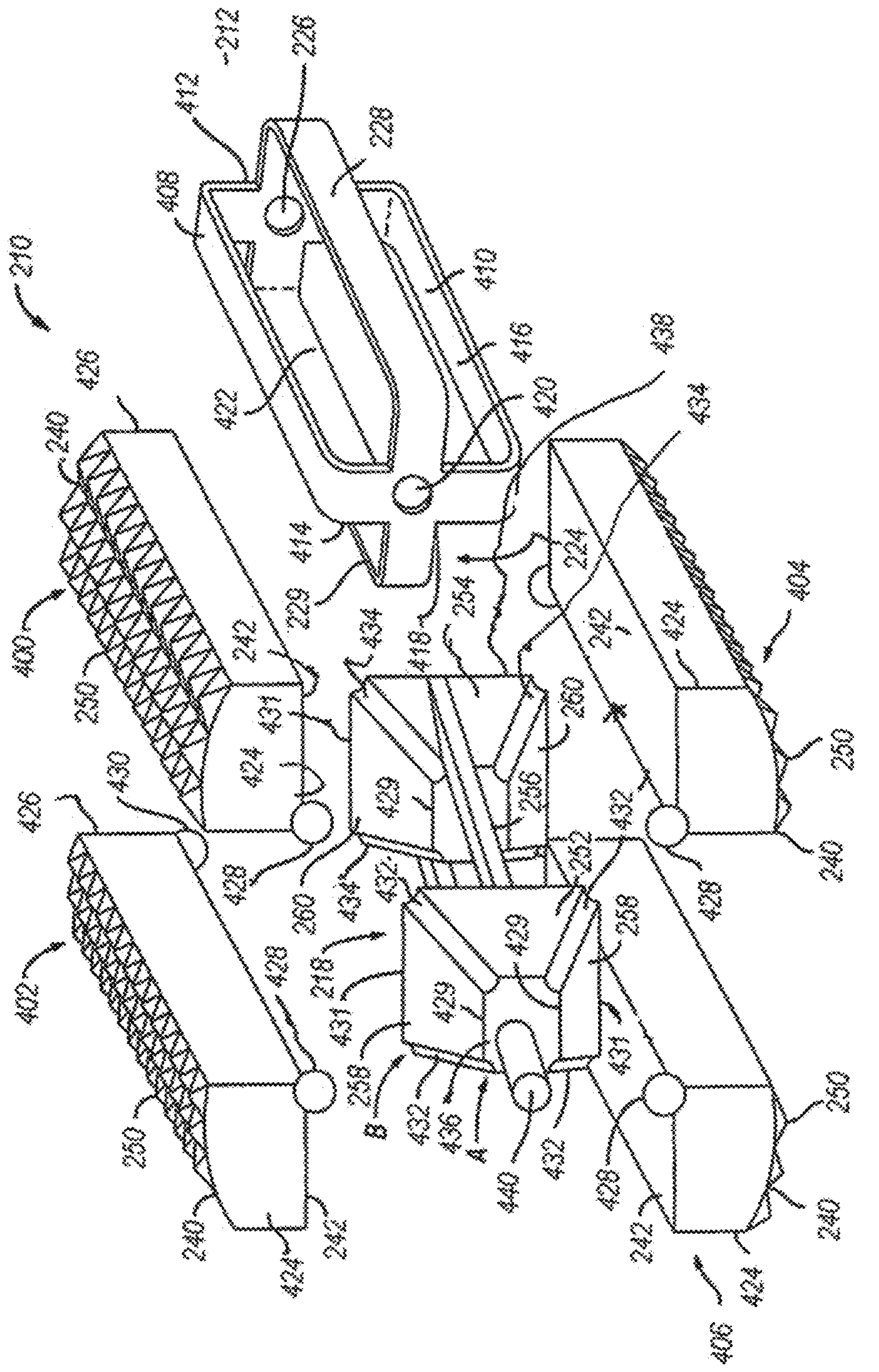
FIG. 28 is an exploded perspective view of another embodiment of an expandable fusion device.

With reference to FIG. 28, an exploded perspective view of another embodiment of fusion device 210 is shown. In an exemplary embodiment, the fusion device 210 includes a body portion 212, a first endplate 400, a second endplate 402, a third endplate 404, a fourth endplate 406, and a translation member 218. In this embodiment, the fusion device 210 is configured to expand both vertically and laterally.

In an exemplary embodiment, the body portion 212 has a first end 224, a second end 226, a first side portion 228 connecting the first end 224 and the second end 226, and a second side portion 229 on the opposing side of the body portion 212 connecting the first end 224 and the second end 226. The body portion 212 further includes a top side portion 408 connecting the first end 224 and the second end 226, and a bottom side portion 410 on the opposing side of the body portion 212 connecting the first end 224 and the second end 226. The body portion 212 further includes first gap 412 between the top side portion 408 and the first side portion 228, which is sized to receive at least a portion of the first endplate 400. The body portion 212 further includes second gap 414 between the top side portion 408 and the second side portion 229, which is sized to receive at least a portion of the second endplate 402. The body portion 212 further includes third gap 416 between the bottom side portion 410 and the first side portion 228, which is sized to receive at least a portion of the third endplate 404. The body portion 212 further includes fourth gap 418 between the bottom side portion 410 and the second side portion 229, which is sized to receive at least a portion of the fourth endplate 406.

The first end 224 of the body portion 212, in an exemplary embodiment, includes an opening 420. The opening 420 extends from the first end 224 of the body portion 212 into a central opening 422. In one embodiment, the central opening 422 is sized to receive the translation member 218. The second end 226 of the body portion 212, in an exemplary embodiment, includes an opening 236, which extends from the second end 226 of the body portion 212 into the central opening 422.

Figure 29:
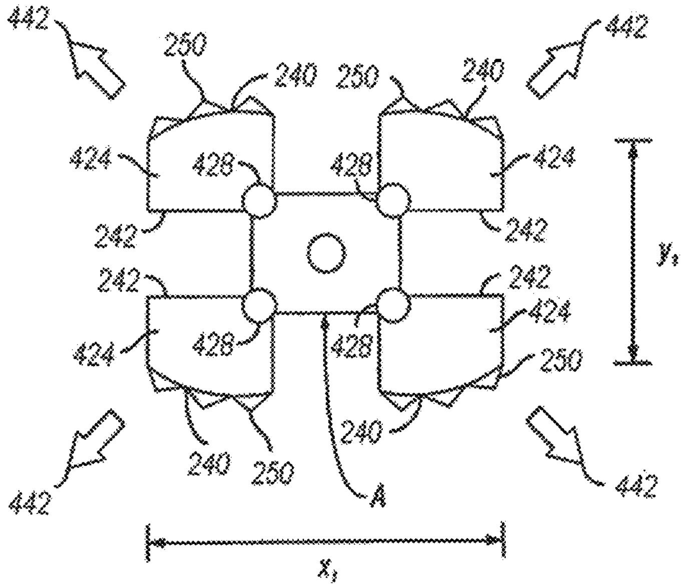
FIG. 29 is an end view of the expandable fusion device of FIG. 28 in an unexpanded position.
Figure 30:
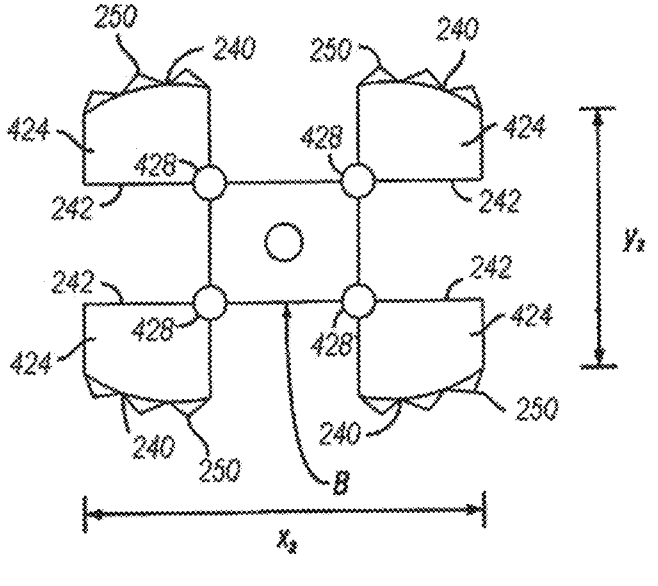
FIG. 30 is an end view of the expandable fusion device of FIG. 28 in an expanded position.

Although the following discussion relates to the first endplate 400, it should be understood that it also equally applies to the second endplate 402, the third endplate 404, and the fourth endplate 406, as these endplates 402, 404, 406 are substantially identical to the first endplate 400 in embodiments of the present invention. Turning now to FIGS. 28-30, in an exemplary embodiment, the first endplate 14 has a first end 424 and a second end 426. The first endplate further includes an upper surface 240 connecting the first end 424 and the second end 426 and a lower surface 242 on an opposing side of the endplate 400 connecting the first end 424 and the second end 426. While not illustrated, the first endplate 214 may include a through opening sized to receive bone graft or similar bone growth inducing material and further allow the bone graft or similar bone growth inducing material to be packed in the central opening 422 in the body portion 212.

In one embodiment, the lower surface 242 includes at least one first retaining socket 428 on the lower surface 242. In an exemplary embodiment, the lower surface 242 includes a first retaining socket 428 at the interior corner of the intersection of the first end 424 and the lower surface 242, and a second retaining socket 430 at the interior corner of the intersection of the first end 424 and the lower surface 242.

Referring now to FIGS. 28-30, in one embodiment, the upper surface 240 of the first endplate 400 is curved convexly. Alternatively, the upper surface 240 is flat or curved concavely to allow for a greater or lesser degree of engagement with the adjacent vertebral body 2 (shown on FIG. 1, for example). It is also contemplated that the upper surface 240 can be generally planar but includes a generally straight ramped surface or a curved ramped surface. The ramped surface allows for engagement with the adjacent vertebral body 2 in a lordotic fashion. In an exemplary embodiment, the upper surface 240 includes texturing 250 to aid in gripping the adjacent vertebral bodies. Although not limited to the following, the texturing can include teeth, ridges, friction increasing elements, keels, or gripping or purchasing projections.

With reference to FIG. 28, in an exemplary embodiment, the translation member 218 is sized to be received within the central opening 422 of the body portion 212. The translation member 218 should be sized to allow longitudinal translation within the central opening 422. In an embodiment, the translation member 218 includes at least a first expansion portion 252. In another embodiment, the translation member 218 includes a first expansion portion 252 and a second expansion portion 254, the expansion portions 252, 254 being connected together via a bridge portion 256. It is also contemplated that there may be more than two expansion portions where each of the expansion portions is connected by a bridge portion. The expansion portions 252, 254 each have angled surfaces 258, 260. In an embodiment, the angles surfaces 258, 260 each comprise first end 229 and second end 231 with second end 231 being wider than the first end 229. In an exemplary embodiment, the expansion portions 252, 254 include grooved portions 432, 434 on the edges of at least two sides (e.g., the lateral sides) of the angled surfaces 258, 260. The grooved portions 432, 434 are configured and dimensioned to engage the first and second retaining sockets 428, 430 on the endplates 400, 402, 404, 406. In an exemplary embodiment, the grooved portions 432, 434 retain the first and second retaining sockets 428, 430 in sliding engagement.

In one embodiment, the translation member 218 includes a first end 436 and a second end 438. The first end 436 of the translation member includes an extension 440 sized to be received within the opening 420 in the first end 224 of the body portion 212. While not illustrated, the second end 438 also can include a similar extension sized to be received within opening 232 in the second end 226 of the body portion 212.

The expandable fusion device 210 of FIGS. 28-30 can be inserted into the intervertebral space in a manner similar to that the previously described with respect to FIGS. 15-19. After insertion, the expandable fusion device 210 of FIGS. 28-30 can be expanded into the expanded position. As previously mentioned, the fusion device 210 shown on FIGS. 28-30 expands both vertically and laterally. To expand the fusion device 210, the translation member 218 can be moved with respect to the body portion 212 toward the first end 224 of the body portion. An instrument can be used, in an exemplary embodiment. As the translation member 218 moves, the first retaining socket 428 and the second retaining socket 430 ride along the grooved portions 432, 434 of the expansion portions 252, 254 pushing the endplates 400, 402, 404, 406 outwardly in the direction indicated by arrows 442. In an embodiment, the endplates 400, 402, 404, 406 move outwardly in an oblique fashion to expand the fusion device 210 both vertically and laterally. The expanded configuration of the expansion device 210 is best seen in FIG. 30.

After expansion, the expandable fusion device 210 can be contracted back to the unexpanded configuration. The unexpanded configuration of the fusion device 210 is best seen in FIG. 29. To contract the fusion device 210, the translation member 218 is moved with respect to the body portion 212 toward the second end 226 of the body portion 212. As the translation member 218 moves, the first retaining socket 428 and the second retaining socket 430 ride along the grooved portions 432, 434 of the expansion portions 252, 254 pulling the endplates 400, 402, 404, 406 inwardly in a direction opposite that indicated by arrows 442. In an embodiment, the endplates 400, 402, 404, 406 move inwardly in an oblique fashion to contract the fusion device 210 both vertically and laterally.

Figure 31:
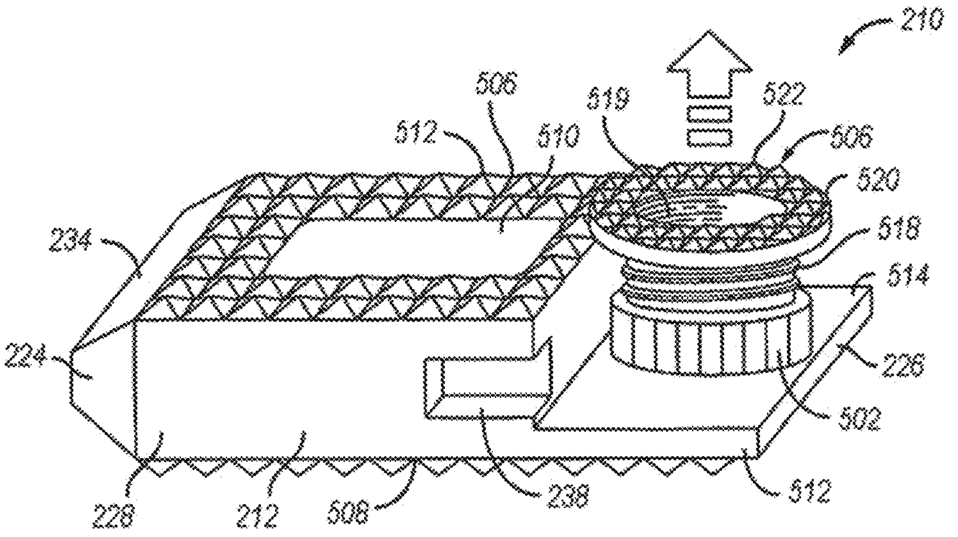
FIG. 31 is a perspective view of another embodiment of an expandable fusion device.
Figure 32:
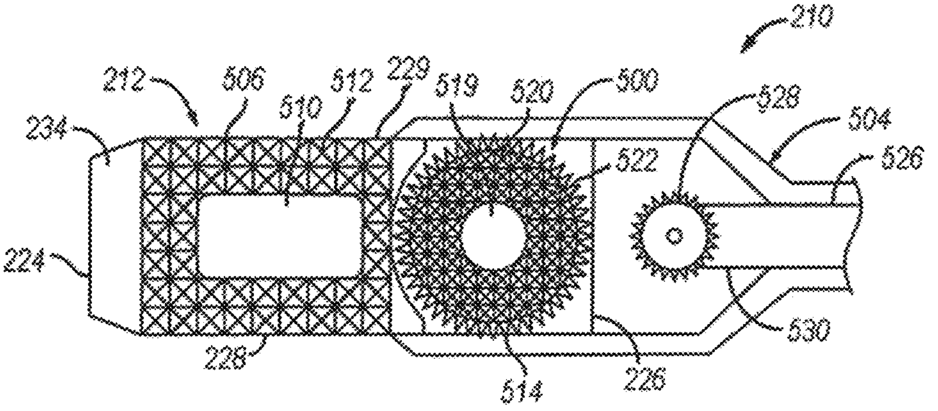
FIG. 32 is a top view of the expandable fusion device of FIG. 31.

With reference to FIGS. 31-32, another embodiment of expandable fusion device 210 is shown. In an exemplary embodiment, the fusion device 210 includes a body portion 212, a vertically expanding plate 500, and a gear 502. In this embodiment, a portion of the fusion device 210 is configured to expand vertically in at least one direction. In an exemplary embodiment, the vertically expanding plate 500 is configured to expand outwardly from the body portion 212. It is contemplated that an expandable fusion device 210 may be used to correct spinal curvature due to, for example, scoliosis, lordosis, and the like.

In an exemplary embodiment, the body portion 212 has a first end 224, a second end 226, a first side portion 228 connecting the first end 224 and the second end 226, and a second side portion 229 on the opposing side of the body portion 212 connecting the first end 224 and the second end 226. The first end 224 of the body portion 212, in an exemplary embodiment, includes at least one angled surface 234, but can include multiple angled surfaces. The angled surface 234 can serve to distract the adjacent vertebral bodies when the fusion device 210 is inserted into an intervertebral space. In another preferred embodiment, it is contemplated that there are at least two opposing angled surfaces forming a generally wedge shaped to distract the adjacent vertebral bodies when the fusion device 210 is inserted into an intervertebral space. In yet another preferred embodiment, first side portion 228 and second side portion 229 each include a recess 238 located towards the second end 226 of the body portion 212. The recess 238 is configured and dimensioned to receive an insertion instrument 504 that assists in the insertion of the fusion device 210 into an intervertebral space.

In an exemplary embodiment, the body portion 212 includes an upper engagement surface 506 extending from the first end 224 towards the second end 226, and a lower engagement surface 508 extending between the first end 24 and the second end 26. In an embodiment, the upper engagement surface 506 has a through opening 510. Although not illustrated, the lower engagement surface 508 may have a through opening that is similar to through opening 510. The through opening 510, in an exemplary embodiment, is sized to receive bone graft or similar bone growth inducing material and further allow the bone graft or similar bone growth inducing material to be packed in the central opening in the body portion 212. In an embodiment, at least a portion of the body portion 212 is removed to form a landing 512 in the body portion 212. In an exemplary embodiment, a portion of the upper engagement surface 506 and the second end 226 are removed to form the landing 512 having an upper surface 514. While not illustrated, a portion of the lower engagement surface 508 and the second end 226 may be cut away, in an alternative embodiment, to form the landing 512.

Figure 34:
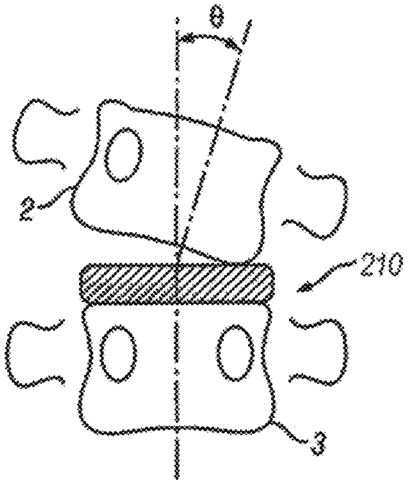
FIG. 34 is a front view of the expandable fusion device of FIG. 33 shown between adjacent vertebrae in an unexpanded position.

In one embodiment, the upper engagement surface 506 and the lower engagement surface 508 are flat and generally planar to allow engagement surfaces 506 to engage with the adjacent vertebral body 2 (shown on FIG. 34, for example) and the lower engagement surface 508 to engage with the adjacent vertebral body 3 (shown on FIG. 34, for example). Alternatively, the upper engagement surface 506 and/or the lower engagement surface 508 can be curved convexly or concavely to allow for a greater or lesser degree of engagement with the adjacent vertebral bodies 2, 3. In an exemplary embodiment, the upper engagement surface 506 and/or the lower engagement surface includes texturing 512 to aid in gripping the adjacent vertebral bodies. Although not limited to the following, the texturing can include teeth, ridges, friction increasing elements, keels, or gripping or purchasing projections.

In an exemplary embodiment, vertically expanding plate 500 is coupled to an end of threaded bolt 518, which is coupled to the gear 502. In one embodiment, the threaded bolt 518 is in threaded engagement with the gear 502. In an alternative embodiment, a bolt having ratchet teeth may be used instead of threaded bolt 518. In an embodiment, the gear 502 is coupled to the landing 512. In one embodiment, the gear 502 is rotatably coupled to the landing 512.

Figure 33:
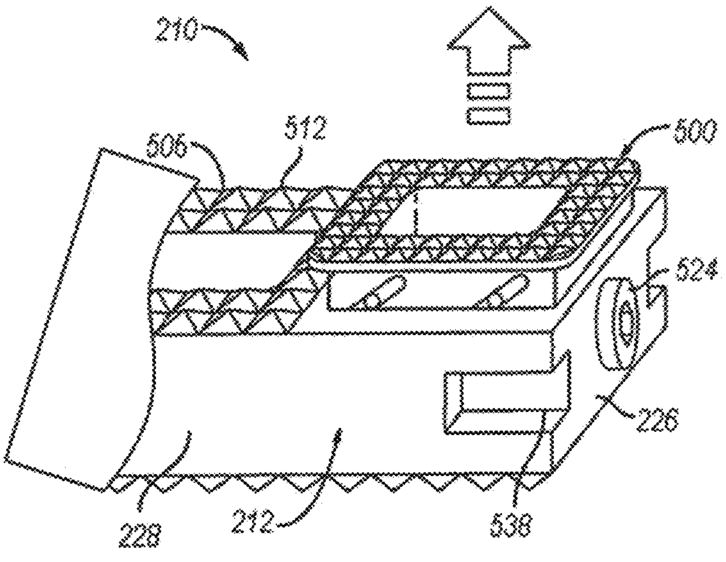
FIG. 33 is a perspective view of the expandable fusion device of FIG. 31 with a closed end.

The vertically expanding plate 500 includes a through bore 519 and an upper surface 520. In one embodiment, the vertically expanding plate 500 is generally circular in shape. Other suitable configurations of the expanding plate 500 may also be suitable. In an embodiment, the vertically expanding plate may be generally rectangular in shape with rounded corners, as best seen in FIG. 33. In one embodiment, the vertically expanding plate 500 is flat and generally planar to allow upper surface 520 to engage with the adjacent vertebral body 2. Alternatively, the upper surface 520 can be curved convexly or concavely to allow for a greater or lesser degree of engagement with the adjacent vertebral bodies. In an exemplary embodiment, the upper surface 520 includes texturing 522 to aid in gripping the adjacent vertebral bodies. Although not limited to the following, the texturing can include teeth, ridges, friction increasing elements, keels, or gripping or purchasing projections.

With reference to FIG. 33, an alternative embodiment of the expandable fusion device 210 of FIGS. 31-32 is shown. In this embodiment, the gear 502 is enclosed within the body portion 212 towards the second end 226 of the body portion 212 with the vertically expanding plate 500 disposed at or above the upper engagement surface 506 of the body portion 212. In an embodiment, the vertically expanding plate 500 is positioned towards the second end 226 of the body portion 212. While not illustrated, the threaded bolt 518 extends through the upper engagement surface 506 and couples the vertically expanding plate 500 and the gear 502. An actuator screw 524 extends through the first end 224 of the body portion 212 to engage the gear 502.

Figure 35:
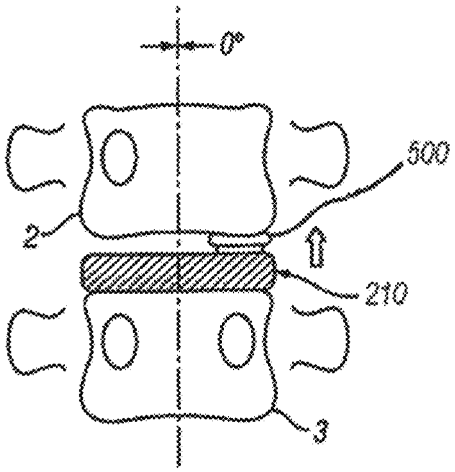
FIG. 35 is a front view of the expandable fusion device of FIG. 33 shown between adjacent vertebrae in an expanded position.

The expandable fusion device 210 of FIGS. 31-33 can be inserted in the intervertebral space in a manner similar to that the previously described with respect to FIGS. 15-19. FIG. 34 illustrates the expandable fusion device 210 of FIG. 33 between adjacent vertebral bodies 3, 4 in an unexpanded position. After insertion, the expandable fusion device 210 of FIGS. 31-33 can be expanded into the expanded position. As previously mentioned, a portion of the fusion device shown on FIGS. 31-33 expands vertically in at least one direction. To partially expand the fusion device 210, the gear 502 can be rotated in a first direction. An instrument 526 having a gear 528 disposed on a distal end 530 of the instrument may be used to rotate the gear 502, as best seen on FIG. 32. In another embodiment, an instrument (not illustrated) may be used to rotate actuation member 524 in a first direction. As discussed above, the actuation member 524 is engaged with gear 502; thus, as the actuation member 524 is rotated in first direction, the gear 502 rotated in a first direction. The embodiment with the actuation member 524 is best seen in FIG. 33. As the gear 502 rotates, the threaded bolt 518 extends outward from the gear 502, thus extending the laterally expanding plate 500 outward from the body portion 212. FIG. 35 illustrates the expandable fusion device 210 of FIG. 33 in an expanded position.

After expansion, the expandable fusion device 210 can be contracted back to the unexpanded position. The unexpanded position of the fusion device 210 is best seen in FIG. 34. To contract the fusion device 210, the gear 502 is rotated in a second direction that is opposite the first direction. The instrument 526 with the gear 528 may be used to rotate the gear 502. Alternatively, an instrument may be used to rotate the actuation member 524 to turn the gear 502 in the second direction. As the gear 502 rotates in the second direction, the threaded bolt 518 retracts pulling the laterally expanding plate 500 inward into the unexpanded position.

Figure 36:
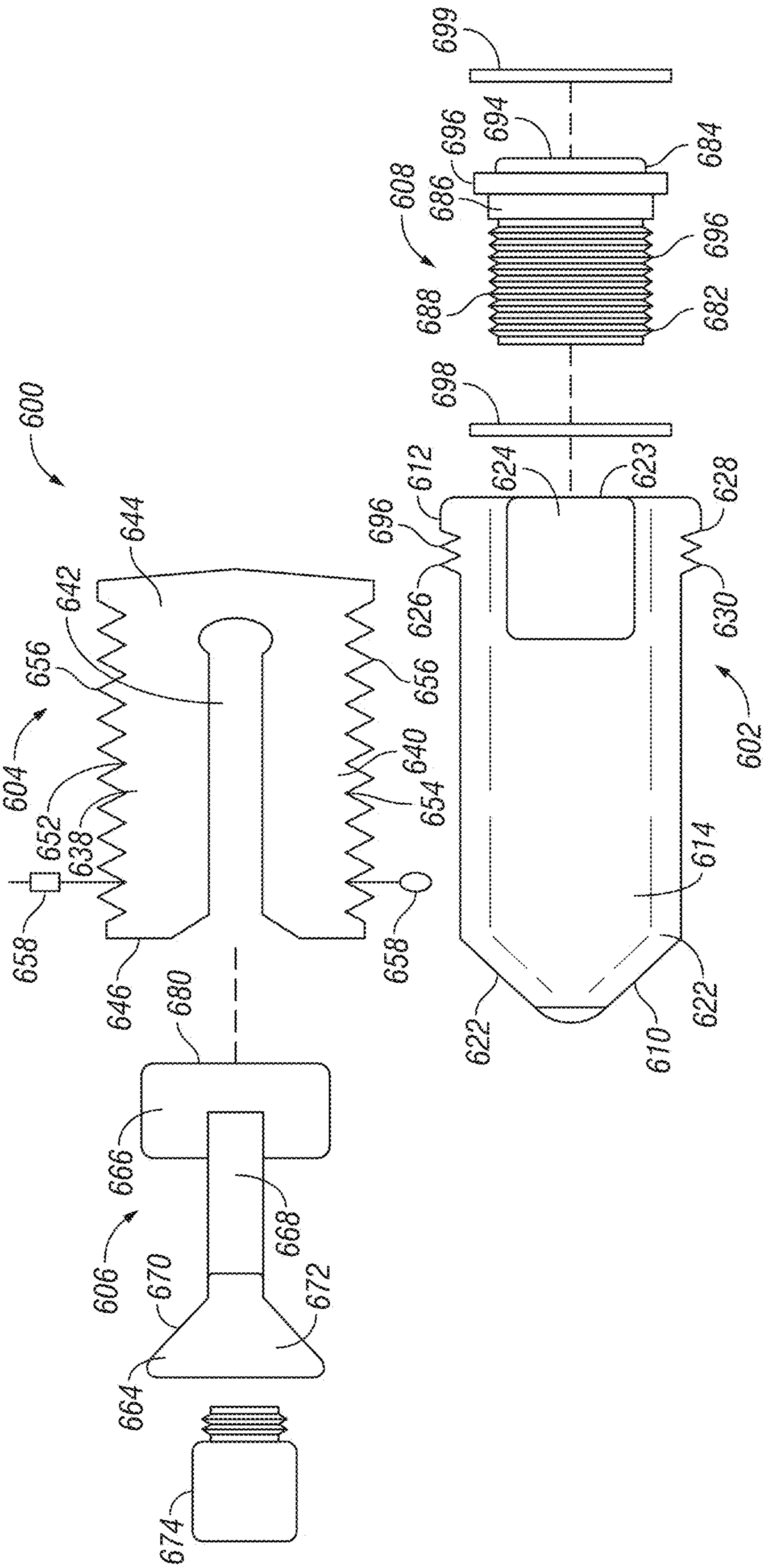
FIG. 36 is an exploded view of another embodiment of an expandable fusion device according to the present invention.
Figure 37:
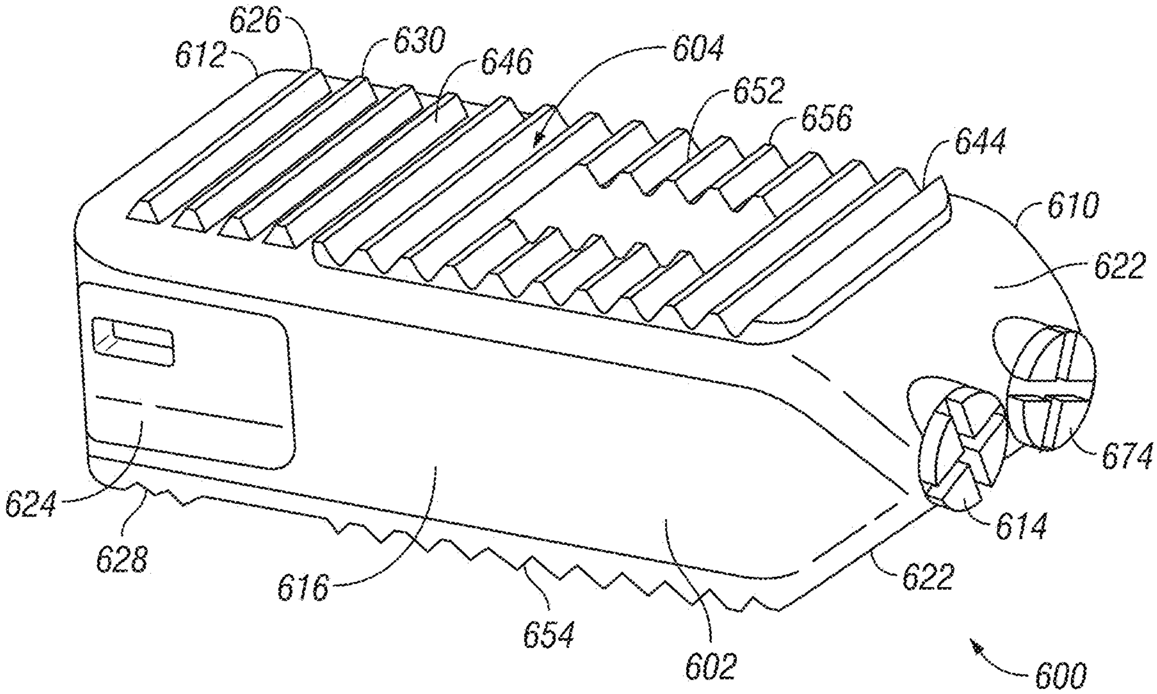
FIG. 37 is a front perspective of the expandable fusion device of FIG. 36.

With reference now to FIGS. 36 and 37, an alternative embodiment of an expandable fusion device 600 is shown. In an exemplary embodiment, the expandable fusion device 600 includes a body portion 602, an expandable member 604, a ramped translation member 606, and an actuation member 608. In accordance with present embodiments, the expandable fusion device 600 is configured for angled expansion (also referred to herein as "lordotic" expansion). Angled expansion of the expandable fusion device 600 may beneficial, for example, to introduce or even increase lordosis in the spine. By increasing lordosis, sagittal balance may be restored, in some embodiments.

With additional reference to FIGS. 38-41 and 43, the body portion 602 will now be described in more detail in accordance with example embodiments. As illustrated, the body portion 602 has an anterior end 610 and a posterior end 612. A first side portion 614 and a second side portion 616 may connect the anterior end 610 and the posterior end 612. As best seen on FIG. 43, the body portion 602 may be generally hollow with the anterior end 610, the posterior end 612, the first side portion 614, and the second side portion 616 defining an internal cavity 618 that has an upper window 620 and a lower window (not shown). In one embodiment, the internal cavity 618 is sized to receive the expandable member 604.

The anterior end 610 of the body portion 602, in an exemplary embodiment, includes one or more angled surfaces 622, but can include multiple angled surfaces. The angled surfaces 622 can serve to distract adjacent vertebral bodies 3, 4 (e.g., shown on FIG. 1) when the fusion device 600 is inserted into intervertebral spaces. In another preferred embodiment, it is contemplated that there at least two opposing angled surfaces 622 forming a generally wedge shape to distract the adjacent vertebral bodies when the fusion device 10 is inserted into an intervertebral space.

The posterior end 612 of the body portion 602, in an exemplary embodiment, includes an opening 623, such as a cylindrical bore, for example. The opening 623 may extend from the posterior end 612 into the internal cavity 618 in the body portion 602. In one embodiment, the opening 623 is sized to receive the actuation member 608. The opening 623 may include a mechanical stop 632 (e.g., a rim, lip, etc.) projecting from an internal surface 634 of the opening. The internal surface 634 may further include an internal groove 636 spaced posteriorly from the mechanical stop 632. In another embodiment, the first and second side portions 614, 616 each include a recess 624 located at or near the posterior end 612 of the body portion 602. The recess 624 may be configured and dimensioned to receive an insertion instrument (not shown) that assists in the insertion of the fusion device 600 into an intervertebral space.

The posterior end 612 of the body portion 602, in an exemplary embodiment, further includes upper and lower bone engagement surfaces 626, 628 at the posterior end 612. The upper and lower bone engagement surfaces 626, 628 may be configured to engage the adjacent vertebral bodies 2, 3 (shown on FIG. 1, for example). In the illustrated embodiment, the upper and lower bone engagement surfaces 626, 628 each include texturing 630 to aid in gripping the adjacent vertebral bodies 2, 3. Although not limited to the following, the texturing can include teeth, ridges, friction increasing elements, keels, or gripping or purchasing projections.

Figure 38:
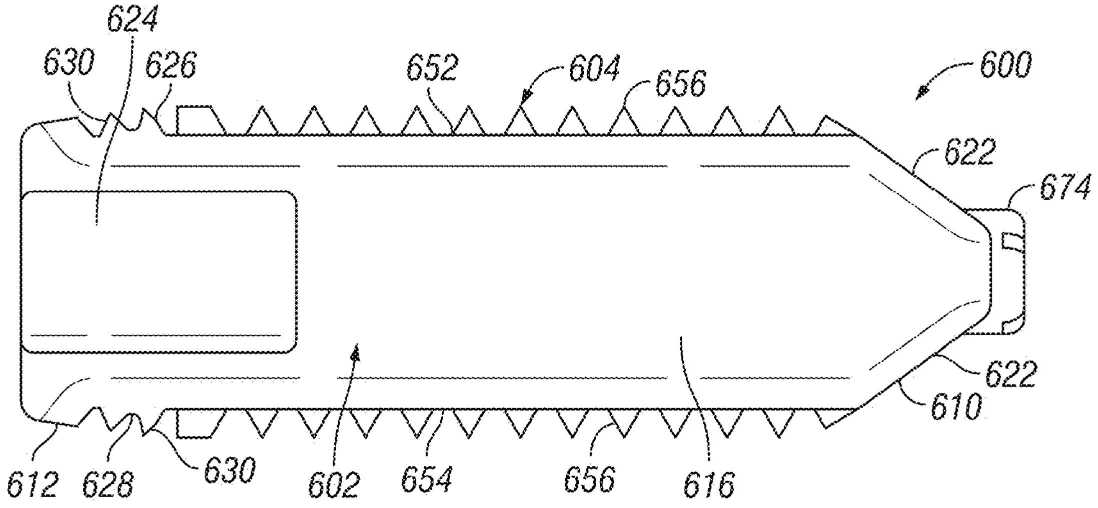
FIG. 38 is a side view of the expandable fusion device of FIG. 36 in an unexpanded configuration.
Figure 39:
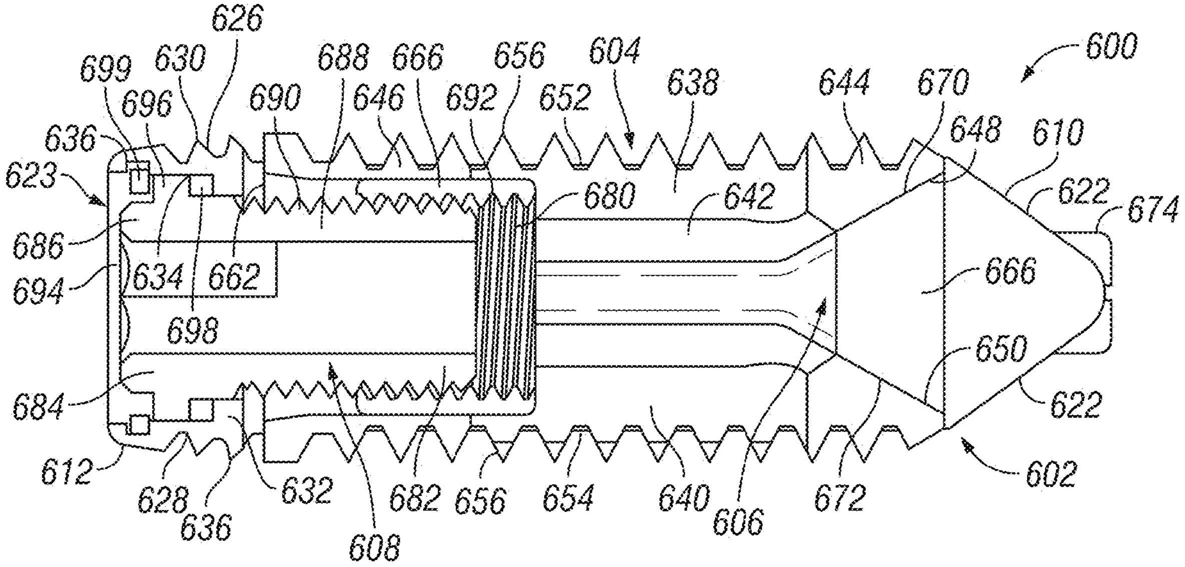
FIG. 39 is a cross-sectional side view of the expandable fusion device of FIG. 36 in an unexpanded configuration.
Figure 40:
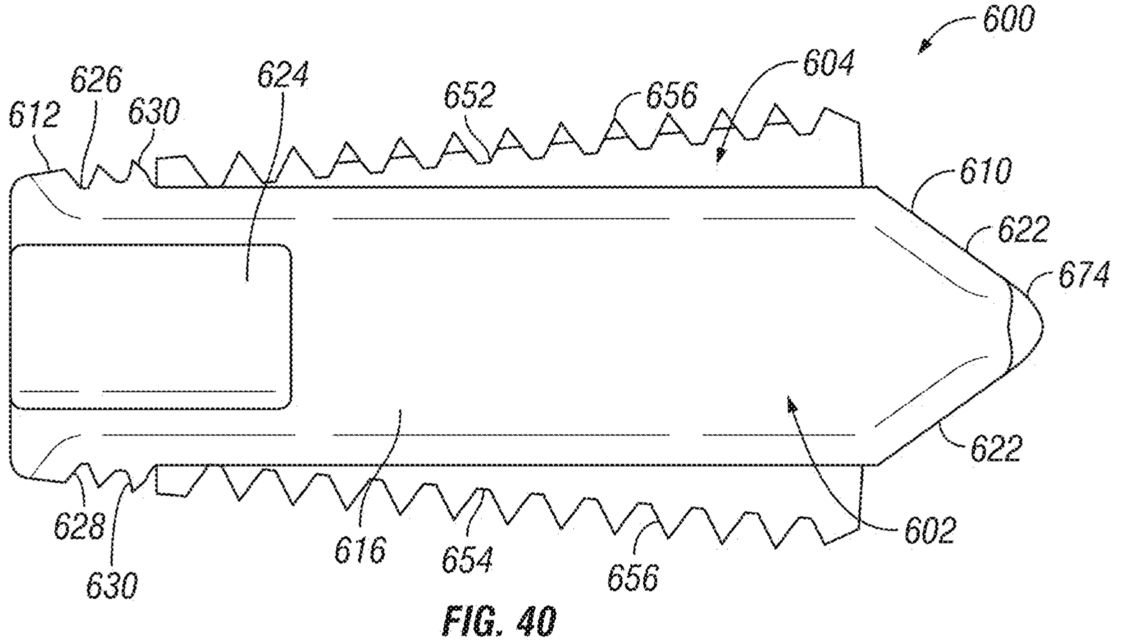
FIG. 40 is a side view of the expandable fusion device of FIG. 36 in an expanded configuration.
Figure 41:
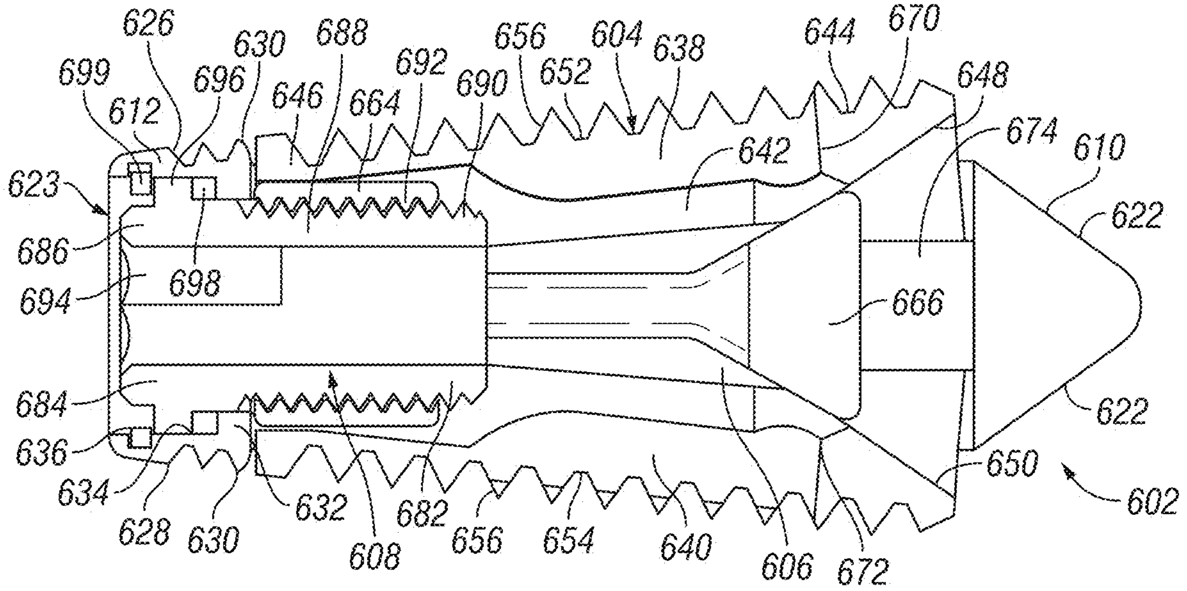
FIG. 41 is a cross-sectional side view of the expandable fusion device of FIG. 36 in an expanded configuration.
Figure 43:
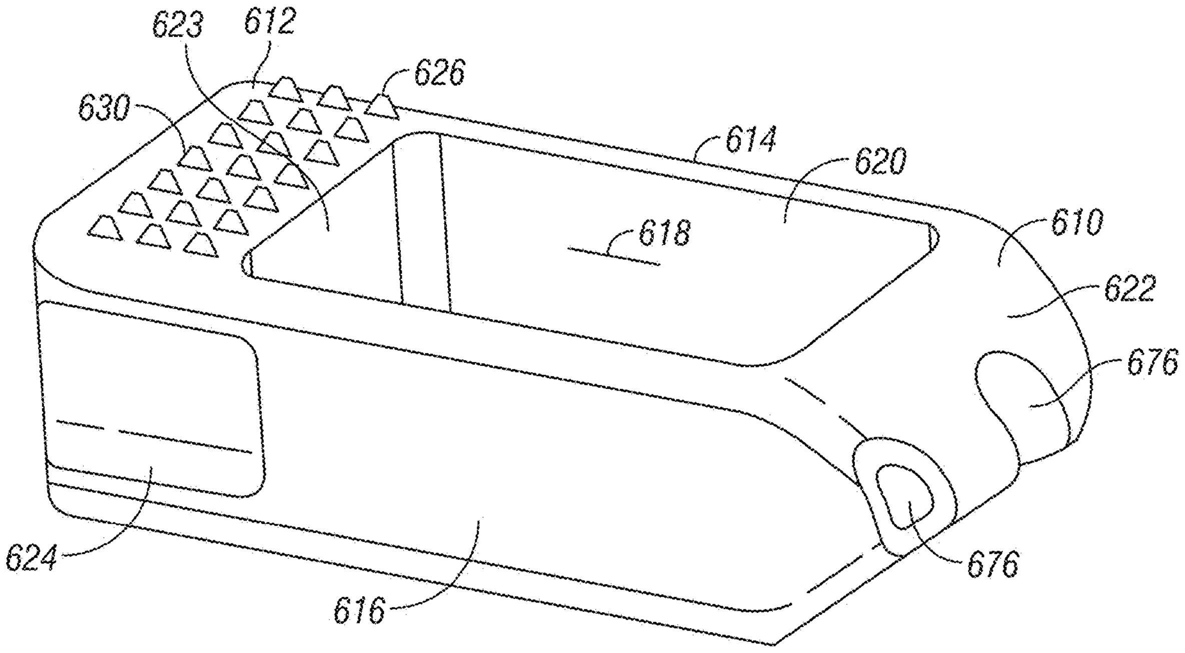
FIG. 43 is a front perspective of the body portion of the expandable fusion device of FIG. 36.

With reference now to FIGS. 36-42, the expandable member 604 will now be described in more detail in accordance with example embodiments. It is contemplated that the expandable member 604 can be made from a flexible material, such as PEEK, or any other biocompatible material such as stainless steel or titanium. However, other materials may also be used for the expandable member 604 in accordance with embodiments of the present invention. As illustrated, the expandable member 604 may include two or more arms, such as first arm 638 and second arm 640, separated by a channel 642. The expandable member 604 may further include a fixed end 644 and an expandable end 646 with the channel 642 running between the first and second arms 638, 640 from the fixed end 644 to the expandable end 646. The first arm 638 and the second arm 640 may be connected at the fixed end 644 which links the first and second arms 638, 640. The first and second arms 638, 640 may move substantially independent from one another at the expandable end 646 while remaining connected at the fixed end 644. As illustrated, the first and second arms 638, 640 may be separated by the channel 642. In the illustrated embodiment, the channel 642 ends at the fixed end 644 in a slightly larger diameter which acts a hinge during expansion of the fusion device 600. Markers 658 (FIG. 36) may be seated in recesses (such as blind holes 660 shown on FIG. 42) formed in each of the first and second arms 638, 640 to, for example, to assist in imaging of the device, such as fluoroscopy. In addition, the expandable member 604 may also include a posterior opening 662 in the fixed end 644, such as a cylindrical bore, through which the actuation member 608 can extend, as best seen in FIGS. 39 and 41.

Figure 42:
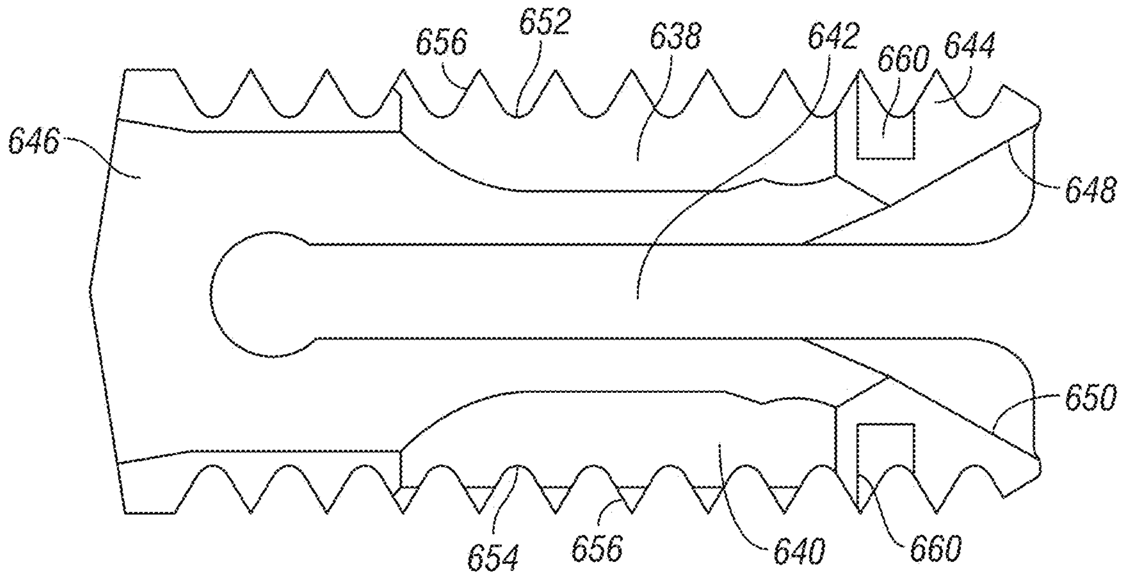
FIG. 42 is a cross-sectional side view of the expandable member of the expandable fusion device of FIG. 36.

As best seen in FIGS. 39, 41, and 42, the first and second arms 638, 640 of the expandable member 604 each include ramped surfaces 648, 650, respectively. In the illustrated embodiment, the ramped surfaces 648, 650 are at or near the expandable end 646. In the illustrated embodiment, the first and second arms 638 each include one ramped surface (e.g., ramped surface 648 and ramped surface 650), but can include any number of ramped surfaces.

In the illustrated embodiment, the first and second arms 638, 640 each include bone engagement surfaces 652, 654, respectively, that face outward. As illustrated, the bone engagement surfaces 652, 654 may be flat and generally planar to allow for engagement of the first and second arms 638 with the adjacent vertebral bodies 3, 4 (e.g., shown on FIG. 1). Alternatively (not illustrated), the bone engagement surfaces 652, 654 may be curved convexly or concavely to allow for a greater or less degree of engagement with the adjacent vertebral bodies 3, 4. It also contemplated that the bone engagement surfaces 652, 654 may be generally planar, but include a generally straight ramped or a curved ramped surface. The ramped surface may allow for an even greater degree of angled expansion. In some embodiments, the bone engagement surfaces 652, 654 may include texturing 656 to aid in gripping the adjacent vertebral bodies 3, 4. Although not limited to the following, the texturing can include teeth, ridges, friction increasing elements, keels, or gripping or purchasing projections.

With reference now to FIGS. 36, 39, and 41, the ramped translation member 606 will now be described in more detail in accordance with example embodiments. As illustrated, the ramped translation member 606 includes a first expansion portion 664 and a second expansion portion 666, the first and second expansion portions 664, 666 being connected by one or more bridge portions 668. It is also contemplated that there may be more than two expansion portions. The first expansion portion 664 may have ramped surfaces 670, 672, which may be dimensioned and configured to engage the ramped surfaces 648, 650 in the expandable end 646 of the expansion member 604. In the illustrated embodiment, the first expansion portion 664 includes two ramped surfaces 670, 672. In the illustrated embodiment, the ramped surfaces 670, 672 of the first expansion portion 664 are rear facing. With additional reference to FIGS. 37 and 43, an embodiment further includes one or more screws 674 that are received in the first expansion portion 664 with the screws 674 being threaded through openings 676 in the posterior end 612 of the body portion 602 to stabilize the ramped translation member 606 in the internal cavity 618 of the body portion 602. The ramped translation member 606, in an exemplary embodiment, may further include an opening 680, such as a cylindrical bore, sized to receive the actuation member 608. In the illustrated embodiment, the opening 680 is disposed in the second expansion portion 666.

With reference to FIGS. 36, 39, and 41, the actuation member 608 will now be described in more detail in accordance with example embodiments. In an exemplary embodiment, the actuation member 608 has a first end 682 and a second end 684. As illustrated, the actuation member 608 may include a head portion 686 at the second end 684 and an extension portion 688 extending from the head portion. Threading 690 disposed on the extension portion 688 should threadingly engage corresponding threading 692 along a portion of the opening 680 of the ramped translation member 606. In another embodiment (not shown), the actuation member 608 may include ratchet teeth instead of the threading 690 with the ratchet teach engaging corresponding ratchet teeth in the opening 680 of the ramped translation member 606. The second end 684 includes a recess 694 dimensioned to receive an instrument (not shown) that is capable of rotating or otherwise moving the actuation member 608.

As illustrated, the head portion 686 of the actuation member 608 may further include a flange 696 or other suitable projection. In some embodiments, the flange 696 of the actuation member 608 may engage the mechanical stop 632 projecting from the interior surface 634 of the opening 623 in the body portion 602. Engagement of the flange 696 with the mechanical stop 632 may restrict forward movement of the actuation member 608 into the opening 623 in the body portion 602. As illustrated, a ring 698 (e.g., a PEEK ring) may be disposed between the mechanical stop 632 and the flange 696 to reduce friction between the actuation member 608 and the body portion 602, for example, when the fusion device 600 is actuated, such as by rotation of the actuation member 608, for example. As further illustrated, a retaining ring 699 may be used to engage the head portion 686 and hold the actuation member 608 in the opening 623 in the body portion 602, for example, preventing threading out of the actuation member 608 when rotated. The retaining ring 699 may be disposed in the internal groove 636 in the opening 623 of the body portion 602, for example. In one embodiment, the retaining ring 699 may be a snap ring.

Turning now to FIGS. 36-41, an example method of installing the expandable fusion device 600 is now discussed. Prior to insertion of the fusion device 600, the intervertebral space is prepared. In one method of installation, a diskectomy is performed where the intervertebral disc, in its entirety, is removed. Alternatively, only a portion of the intervertebral disc can be removed. The endplates of the adjacent vertebral bodies 2, 3 (shown on FIG. 1, for example) are then scraped to create an exposed end surface for facilitating bone growth across the intervertebral space. The expandable fusion device 600 is then introduced into the intervertebral space, with the anterior end 610 of the body portion 602 being inserted first into the disc space followed by the posterior end 612. In an exemplary method, the fusion device 600 is in the unexpanded position when introduced into the intervertebral space. The wedged-shaped of the anterior end 610 in the illustrated embodiment should assist in distracting the adjacent vertebral bodies 2, 3, if necessary. This allows for the option of having little to no distraction of the intervertebral space prior to the insertion of the fusion device 600. In another exemplary method, the intervertebral space may be distracted prior to insertion of the fusion device 600. The distraction provide some benefits by providing greater access to the surgical site making removal of the intervertebral disc easier and making scraping of the endplates of the vertebral bodies 2, 3 easier.

With the fusion device 600 inserted into and seated in the appropriate position in the intervertebral disc space, the fusion device 600 can then be expanded into the expanded position, as best seen in FIGS. 38-41. FIGS. 38 and 39 show the fusion device 600 prior to expansion while FIGS. 40 and 41 show the fusion device 600 in the expanded position. To expand the fusion device 600, an instrument is engaged with the recess 694 in the second end 684 of the actuation member 608. The instrument is used to rotate actuation member 608. As discussed above, actuation member 608 can be engaged (e.g., threadingly engaged) with the ramped translation member 606; thus, as the actuation member 608 is rotated in a first direction, the ramped translation member 606 moves with respect to the body portion 602 toward the posterior end 612 of the body portion 602. In another exemplary embodiment, the ramped translation member 606 is moved in a linear direction with the ratchet teeth engaging as means for controlling the movement of the ramped translation member 606. As the ramped translation member 606 moves, the ramped surfaces 670, 672 of the first expansion portion 664 push against the ramped surfaces 648, 650 in the expandable end 646 of the expandable member 604 pushing the first and second arms 638, 640 outwardly into the expanded position. This can best be seen in FIGS. 40 and 41. Since the expansion of the fusion device 600 is actuated by a rotational input, the expansion of the fusion device 600 is infinite. In other words, the first and second arms 638, 640 can be expanded to an infinite number of heights dependent on the rotational advancement of the actuation member 608.

In the event the fusion device 600 needs to be repositioned or revised after being installed and expanded, the fusion device 600 can be contracted back to the unexpanded configuration, repositioned, and expanded again once the desired positioning is achieved. To contract the fusion device 600, the instrument is engaged with the recess 694 in the second end 684 of the actuation member 608. The instrument is used to rotate actuation member 608. As discussed above, actuation member 608 can be threadingly engaging the ramped translation member 606; thus, as the actuation member 608 is rotated in a second direction, opposite the first direction, the ramped translation member 606 moves with respect to the body portion 602 toward the anterior end 610 of the body portion 602. As the ramped translation member 606 moves, the first and second arms 638, 640 should contract inwardly back into their unexpanded position, for example.

With continued reference to FIGS. 36-41, an example method of assembly the expandable fusion device 600 is now discussed. In accordance with present embodiments, the ramped translation member 606 may be inserted into the expandable member 604. By way of example, the second expansion portion 666 may be inserted into the channel 642 of the expandable member 604 at the expandable end 646 and advanced to the fixed end 644. After insertion of the ramped translation member 606, the expandable member 604 may then be placed into the internal cavity 618 in the body portion 602. For example, the expandable member 604 may be inserted through window (e.g., upper window 620) into the internal cavity 618. As illustrated, the fixed end 644 of the expandable member 604 should be positioned near the posterior end 612 of the body portion 602. The one or more screws 674 may then be inserted through the body portion 602 and into the ramped translation member 606 to, for example, stabilize the ramped translation member 606 preventing rotation. The actuation member 608 may also be inserted into the opening 623 in the posterior end 612 of the body portion and advanced until it is in engagement with the ramped translation member 606. In one embodiment, the actuation member 608 may be advanced into threaded engagement with the opening 680 in the ramped translation member.

In an embodiment, the expandable fusion device 600 can be configured and sized to be placed into an intervertebral disc space between the adjacent vertebral bodies 2 and 3 (shown on FIG. 1, for example) and expanded. In some embodiments, the expandable fusion device 600 may have a width in a range of from about 8 mm to about 22 mm and a length in a range of from about 15 mm to about 65 mm. In further embodiments, the expandable fusion device 600 may have a width in a range of from about 8 mm to about 12 mm and a length in a range of from about 20 mm to about 30 mm. In some embodiments, the expandable fusion device 10 may have an initial height in an unexpanded position in a range of from about 7 mm to about 20 mm and, alternatively from about 7 mm to about 15 mm. In some embodiments, the maximum expansion of the first and second arms 638, 640 at the anterior end 610 of the body portion 602 is about 4 mm or potentially even more.

Figure 44:
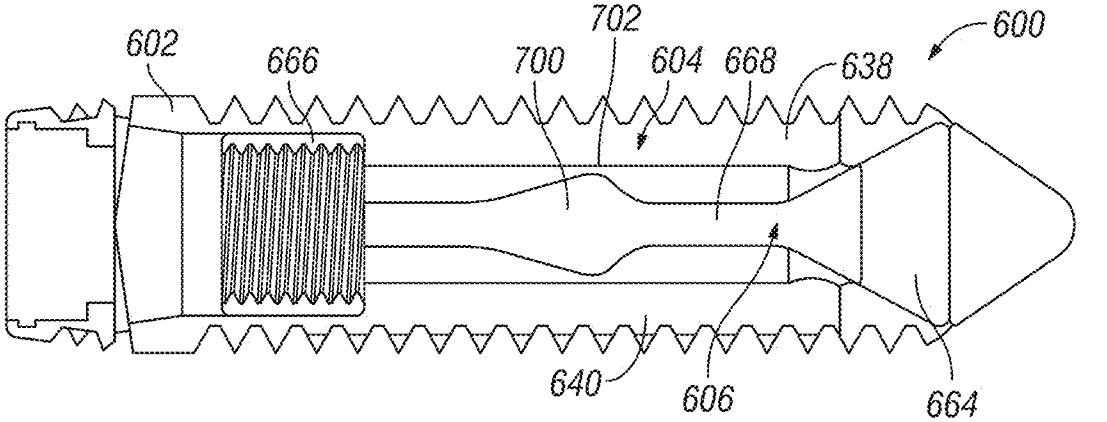
FIG. 44 is a cross-sectional side view of an alternative embodiment of the expandable fusion device of FIG. 36 in an unexpanded configuration.
Figure 45:
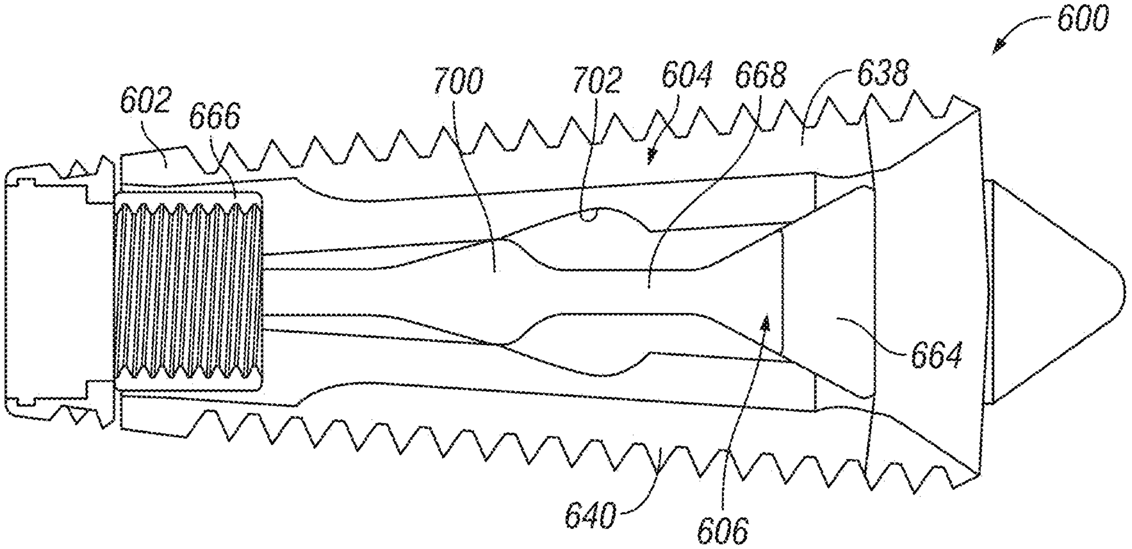
FIG. 45 is a cross-sectional side view of the alternative embodiment of the expandable fusion device shown on FIG. 44.

FIGS. 44 and 45 illustrate an alternative embodiment of the expandable fusion device 600 according to the present invention. For longer configurations of the expandable fusion device 600, the first and second arms 638, 640 may sag or flex, for example, when engaging the adjacent vertebral bodies 3, 4 (shown on FIG. 1, for example). Accordingly, embodiments shown on FIGS. 44 and 45 further include one or more protruding support members 700 on the ramped translation member 606. As illustrated, the protruding support members 700 may be disposed on the one or more of the bridge portions 668 between the first and second expansion portions 664, 666. The protruding support members 700 may engage corresponding recesses 702 in the first and second arms 638, 640. The protruding support members 700 may act to support the first and second arms 638, 640 and prevent undesired flexing during expansion. In alternative embodiments (not shown), the actuation member 608 may engage the expandable member 604 (for example, with a slot and a groove) so that, as the first and second arms 638, 640 expands, the actuation member 608 may engage the expandable member 604 to cause convexity.

Figure 46:
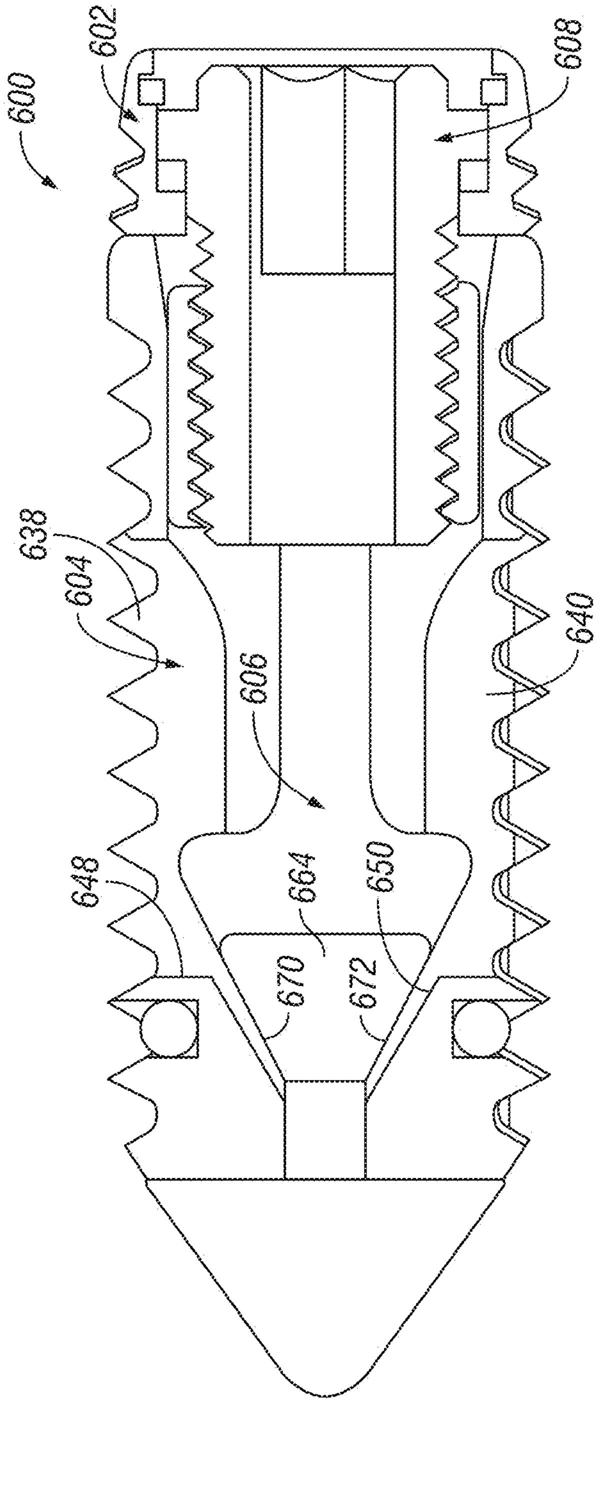
FIG. 46 is a cross-sectional side view of an alternative embodiment of the expandable fusion device of FIG. 36 in an unexpanded configuration.

FIG. 46 illustrates an alternative embodiment of the expandable fusion device 600 according to the present invention. The embodiments illustrated on FIGS. 36-42 illustrate the ramped surfaces 670, 672 on the first expansion portion 664 of the ramped translation member 606 being rear facing. In the embodiment illustrated on FIG. 46, the ramps have been reversed with the ramped surfaces 670, 672 on the first expansion portion 664 being forward facing. Accordingly, the corresponding ramped surfaces 648, 650 on the first and second arms 638, 640 of the expandable member 604 have also been reversed and are shown on FIG.

46 as being rear facing. Accordingly, rotation of the actuation member 608 should move the ramped translation member 606 forward to the anterior end 610 of the body portion 602 such that the ramped surfaces 670, 672 of the ramped translation member 606 push against the ramped surfaces 648, 650 of the first and second arms 638, 640 pushing the first and second arms 638, 640 outwardly into the expanded position.

Figure 47:
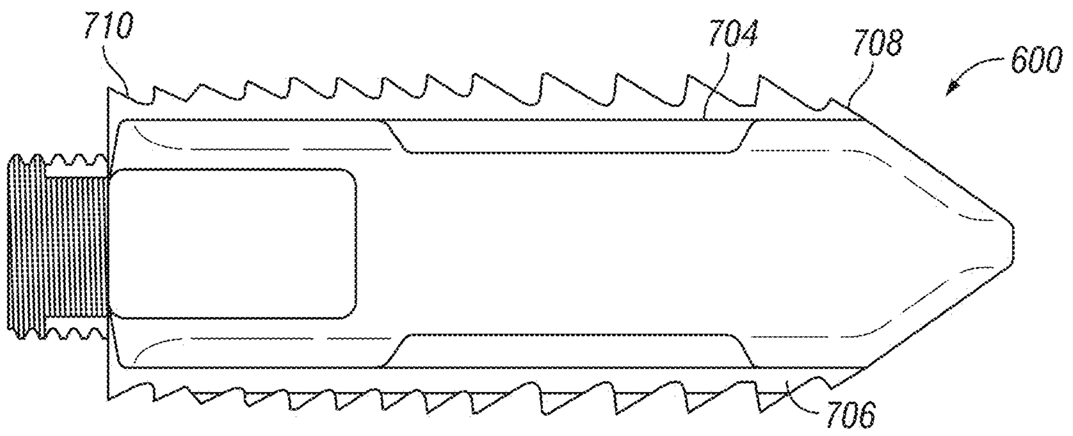
FIGS. 47-58 are side views of an expandable fusion device showing different modes of lordotic expansion.
Figure 48:
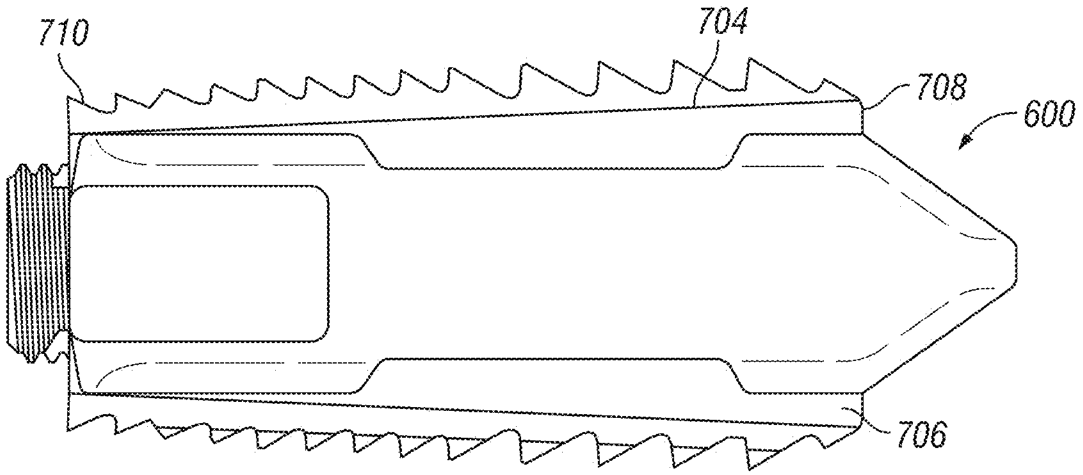
Figure 49:
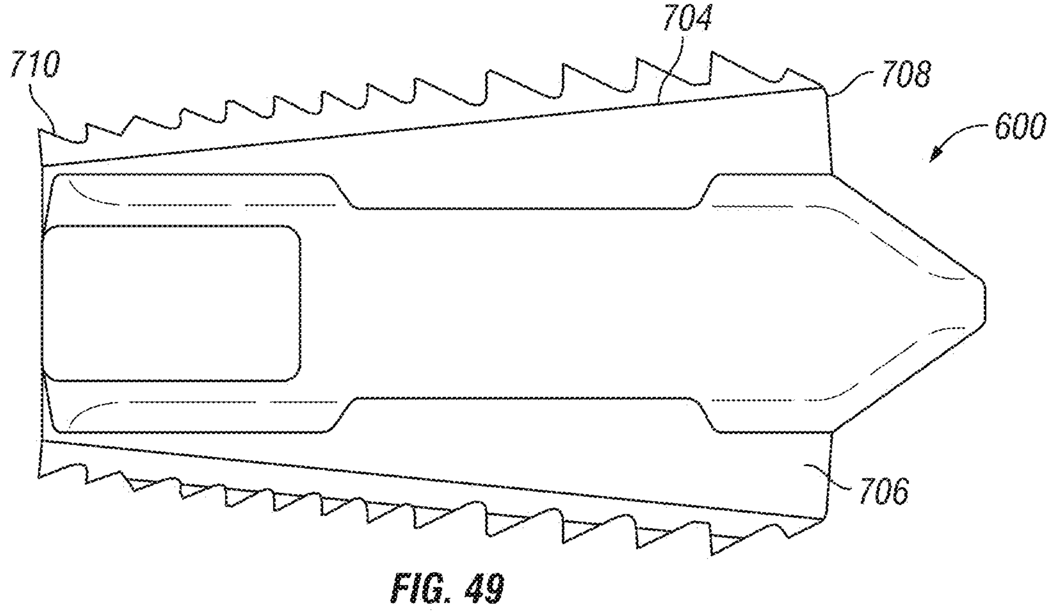
Figure 50:
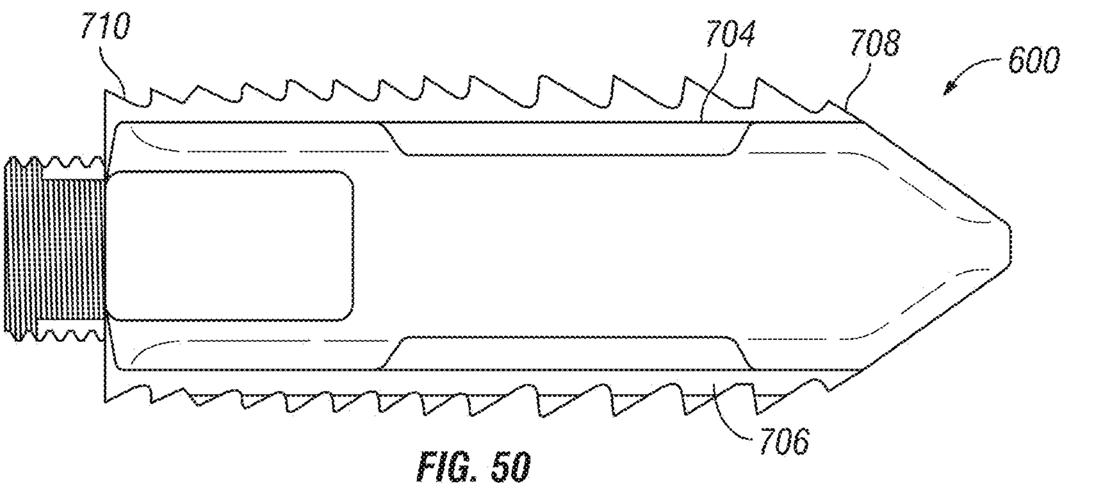
Figure 51:
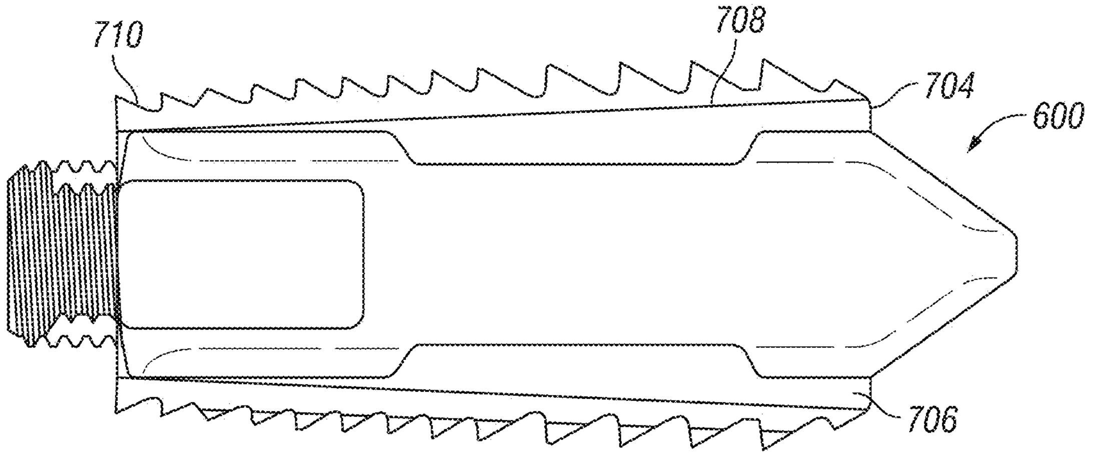
Figure 52:
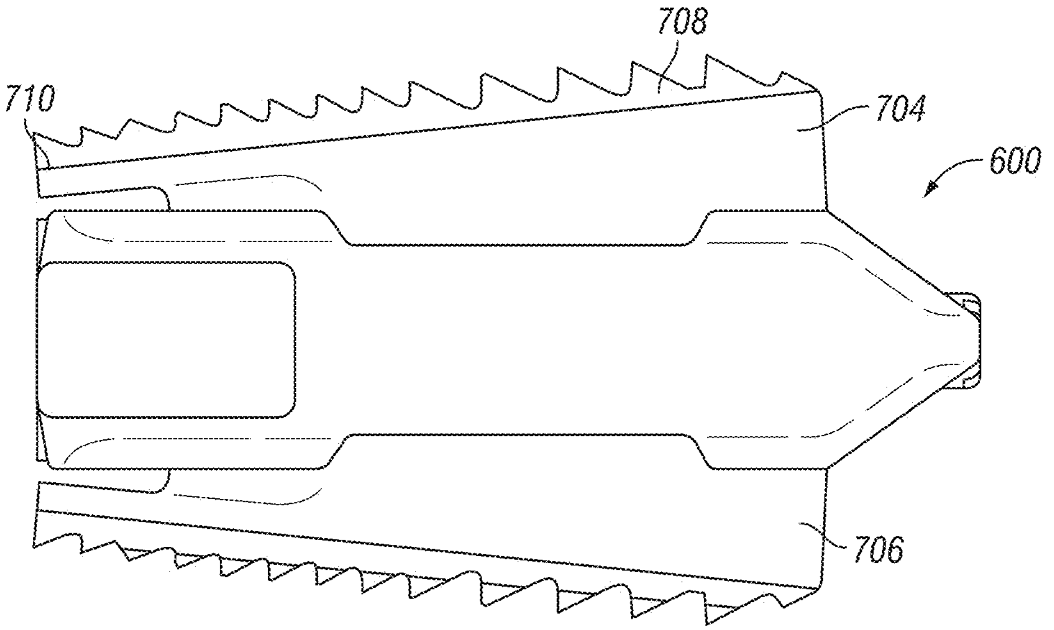
Figure 53:
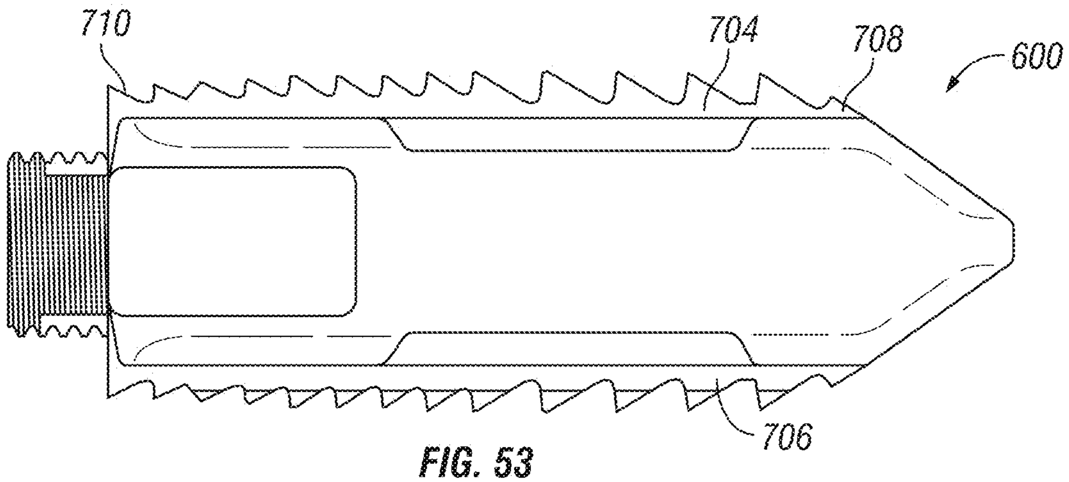
Figure 54:
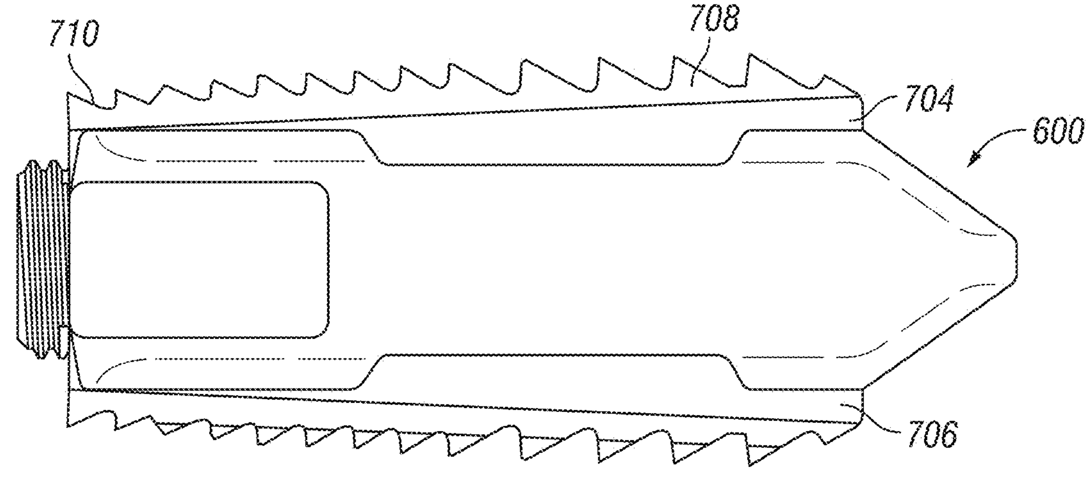
Figure 55:
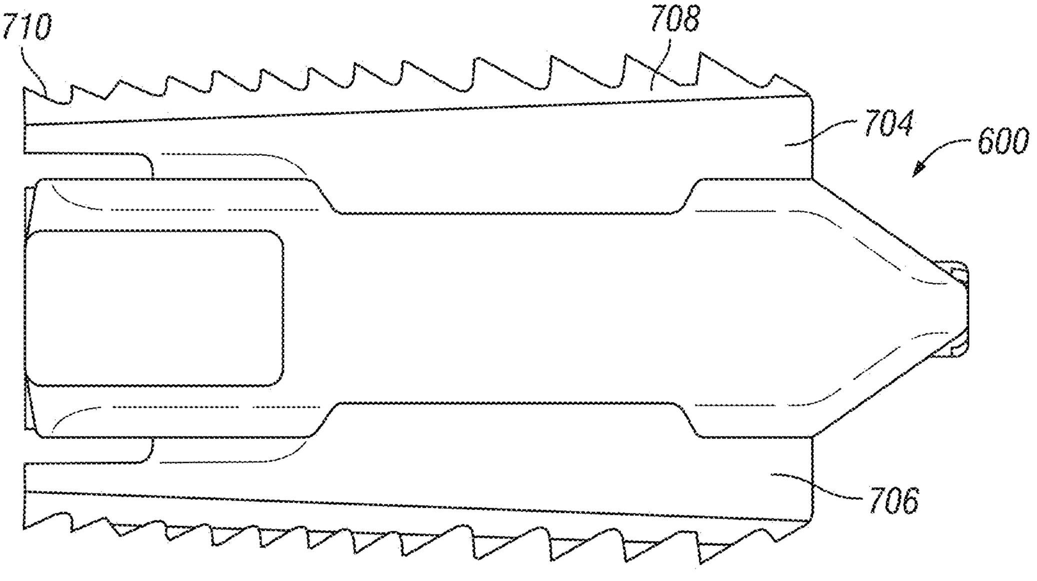
Figure 56:
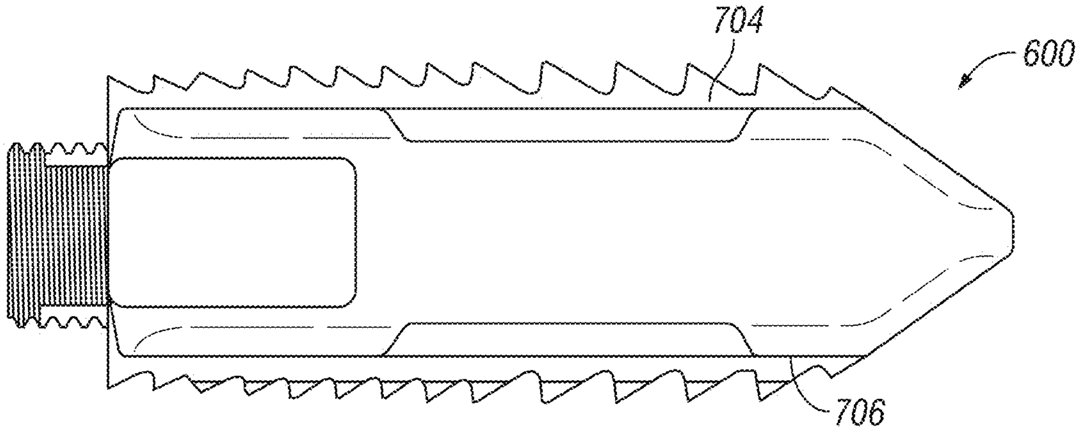
Figure 57:
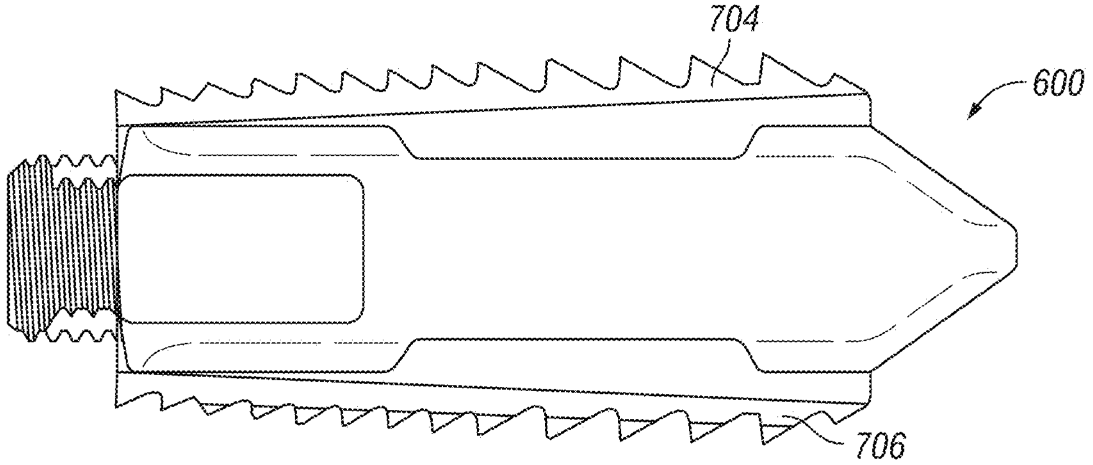
Figure 58:
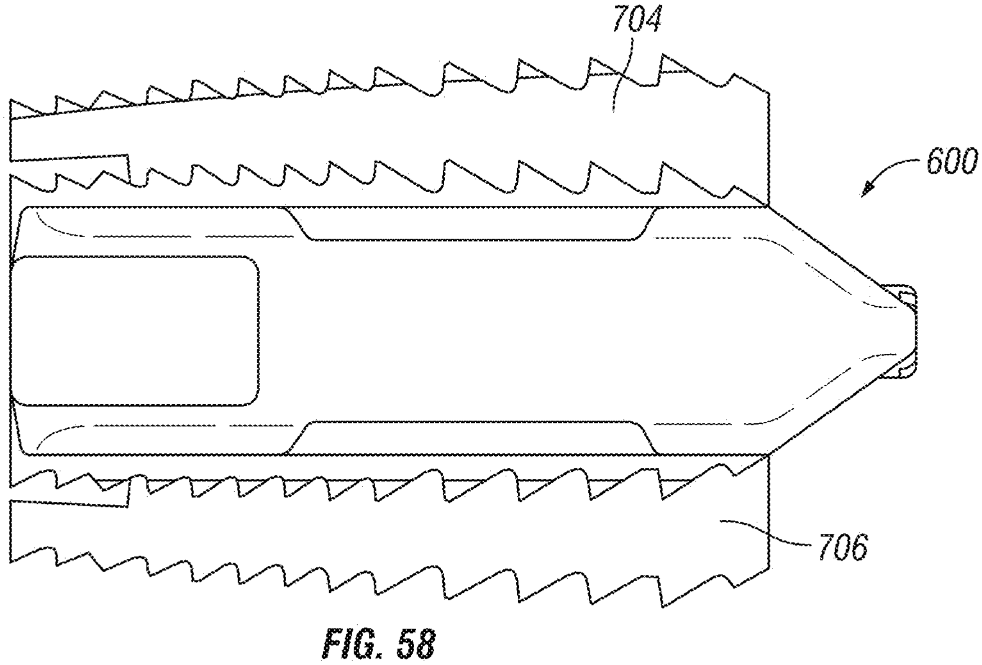

As previously mentioned, embodiments of the expandable fusion devices, such as expandable fusion device 600 shown on FIGS. 36-42 in which the endplates (e.g., endplates 14, 16 or first and second arms 638, 640) may expand into an angled configuration. As illustrated by FIGS. 47-58, the endplates 704, 706 of an expandable fusion device 600 may be expanded in a number of different ways. For example, FIGS. 47-49 illustrate an expandable fusion device 600 in which the endplates 704, 706 only expand at the anterior side 708 while remaining fixed at the posterior side 710. FIGS. 50-52 illustrate an additional example of an expandable fusion device 600 in which the endplates 704, 706 expand at both the anterior side 708 and the posterior side 710 but at different rates. FIGS. 53-55 illustrate yet another example of an expandable fusion device 600 in which the endplates 704, 706 first expand at only the anterior side 708 to achieve lordotic angle followed by expansion at both the anterior side 708 and the posterior side 710 at constant rates to achieve height increase. Advantageously, the embodiment shown on FIGS. 53-55 allows for full angulation without the corresponding height increase. FIGS. 56-58 illustrate yet another example of an expandable fusion device 600. As illustrated, the expandable fusion device 600 has two separate degrees of freedom, allowing for independent angulation and expansion of the endplates 704, 706.

Although the preceding discussion only discussed having a single fusion device (e.g., fusion device 10, fusion device 210, or fusion device 600) in the intervertebral space, it is contemplated that more than one fusion device can be inserted in the intervertebral space. It is further contemplated that each fusion device does not have to be finally installed in the fully expanded state. Rather, depending on the location of the fusion device in the intervertebral disc space, the height of the fusion device may vary from unexpanded to fully expanded.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Although individual embodiments are discussed, the invention covers all combinations of all those embodiments.

What is claimed is:

1. A surgical method comprising:

providing an intervertebral implant including:

a body comprising an opening, a first endplate disposed on an upper side of the body, a second endplate disposed on a lower side of the body, a plurality of pins, a translator coupled to the first and second endplates and comprising at least two expansion portions, an actuator movably coupled to the translator, and a pin member received in an opening of the actuator;

inserting the intervertebral implant into a spinal disc space between two adjacent vertebral bodies; and moving the actuator in a first direction causing the translator to longitudinally translate which causes the first endplate and the second endplate to move from a contracted state to an expanded state, wherein in the contracted state, the first endplate is at a first angle relative to the second endplate, and in the expanded state, the first endplate is at a second angle relative to the second endplate which is greater than the first angle;

wherein the actuator includes a flexible extension received in an opening of the translator and ratchet teeth received in the opening of the body portion, the opening in the body having corresponding ratchet teeth, the flexible extension comprising a plurality of slits and a lip portion, wherein when the pin member is received in the opening of the actuator, the flexible extension is prevented from flexing inwardly thereby preventing the actuator from disengaging from the translator, and wherein the translator receives a portion of each pin and the first and second endplates receive a portion of each pin such that moving the actuator in the first direction causes the translator to move the pins, which causes the first endplate to move in a direction away from the second endplate.

2. The method of claim 1, wherein the first endplate includes first and second spaced apart ramped surfaces whose slopes are different from each other such that opposing ends of the first endplate rise at a different rate relative to the second endplate.

3. The method of claim 2, wherein in the expanded state, the first endplate is in a lordotic position.

4. The method of claim 1, wherein the first endplate includes first and second spaced apart ramped surfaces whose slopes are shaped such that opposing ends of the first endplate rise at the same rate and then rise further at a different rate relative to the second endplate.

5. The method of claim 4, wherein in the expanded state, the first endplate is in a lordotic position.

6. The method of claim 1, wherein each expansion portion includes a curved surface and wherein the first endplate includes a corresponding surface to engage at least the curved surface of one of the expansion portions of the translator and the second endplate includes a corresponding surface to engage at least the curved surface of another of the expansion portions of the translator.

7. The method of claim 1, wherein the first endplate includes at least one extension including at least two openings.

8. The method of claim 7, wherein the body has first and second sides, and the first and second sides include elongate openings.

9. A surgical method comprising:

providing an intervertebral implant including:

a body comprising an opening, a first endplate disposed on an upper side of the body and including a first extension extending downwardly, a second endplate disposed on a lower side of the body and including a second extension extending upwardly, a plurality of pins, a translator coupled to the first and second extensions of the first and second endplates and comprising at least two expansion portions, an actuator movably coupled to the translator; and a pin member received in an opening of the actuator;

inserting the intervertebral implant into a spinal disc space between two adjacent vertebral bodies; and moving the actuator in a first direction causing the translator to longitudinally translate which causes the first endplate and the second endplate to move from a contracted state to an expanded state, wherein in the contracted state, the first endplate is at a first angle relative to the second endplate, and in the expanded state, the first endplate is at a second angle relative to the second endplate which is greater than the first angle;

wherein the actuator includes a flexible extension received in an opening of the translator and ratchet teeth received in the opening of the body portion, the opening in the body having corresponding ratchet teeth, the flexible extension comprising a plurality of slits and a lip portion, wherein when the pin member is received in the opening of the actuator, the flexible extension is prevented from flexing inwardly thereby preventing the actuator from disengaging from the translator, and wherein the translator receives a portion of each pin and the first and second endplates receive a portion of each pin such that moving the actuator in the first direction causes the translator to move the pins, which causes the first endplate to move in a direction away from the second endplate.

10. The method of claim 9, wherein the first endplate extension includes first and second spaced apart ramped surfaces whose slopes are different from each other such that opposing ends of the first endplate rise at a different rate relative to the base.

11. The method of claim 10, wherein in the expanded state, the first endplate is in a lordotic position.

12. The method of claim 9, wherein the first extension of the first endplate includes first and second spaced apart ramped surfaces whose slopes are shaped such that opposing ends of the first endplate rise at the same rate and then rise further at a different rate relative to the second endplate.

13. The method of claim 12, wherein in the expanded state, the first endplate is in a lordotic position.

14. The method of claim 9, wherein each expansion portion includes a curved surface and wherein the first endplate includes a corresponding surface to engage at least the curved surface of one of the expansion portions of the translator and the second endplate includes a corresponding surface to engage at least the curved surface of one another of the expansion portions of the translator.

15. The method of claim 9, wherein the first extension includes at least two openings.

16. The method of claim 15, wherein the body has first and second sides, and the first and second sides include elongate openings.

* * * * *